(12) United States Patent
Tosato et al.

(10) Patent No.: US 7,488,711 B2
(45) Date of Patent: *Feb. 10, 2009

(54) USE OF CALRETICULIN AND CALRETICULIN FRAGMENTS TO INHIBIT ENDOTHELIAL CELL GROWTH AND ANGIOGENESIS, AND SUPPRESS TUMOR GROWTH

(75) Inventors: Giovanna Tosato, Bethesda, MD (US); Sandra E. Pike, Bethesda, MD (US); Lei Yao, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/040,162

(22) Filed: Jan. 20, 2005

(65) Prior Publication Data

US 2005/0208018 A1 Sep. 22, 2005

Related U.S. Application Data

(62) Division of application No. 09/807,148, filed as application No. PCT/US99/23240 on Oct. 5, 1999, now Pat. No. 6,867,180.

(60) Provisional application No. 60/103,438, filed on Oct. 6, 1998.

(51) Int. Cl.
A61K 38/00 (2006.01)
(52) U.S. Cl. .......................................................... 514/2
(58) Field of Classification Search ........................ None
See application file for complete search history.

(56) References Cited

U.S. PATENT DOCUMENTS

| 5,426,097 | A | 6/1995 | Stern et al. |
| 5,591,716 | A | 1/1997 | Siebert et al. |
| 6,596,690 | B2 | 7/2003 | Tosato et al. |

FOREIGN PATENT DOCUMENTS

| CA | 2140814 | 7/1996 |
| WO | WO 89/09273 | 10/1989 |
| WO | WO 95/13828 | 5/1995 |
| WO | WO 96/23001 | 8/1996 |
| WO | WO 96/36643 | 11/1996 |
| WO | WO 00/50080 | 8/2000 |

OTHER PUBLICATIONS

Angiolillo et al., *Leuk Lymphoma* 19(3-4):267-276, 1995.
Araya et al., *Eur Cytokine Netw.* 14:128-33, 2003, abstract only.
Dai et al., *Arteriosclerosis, Thrombosis and Vascular Biology*, 17(11):2359-2368, 1997 (abstract only); Medline abstract No. 1998073667, XP002133012.
Dedhar, *TIBS*, 19:269-271, 1994.
Kishore et al., *Biochem. J.*, 322(2):543-550, 1997 (abstract only); Medline abstract No. 97218114, XP002133013.
Kuwabara et al., *J. Bio. Chem.*, 270(14):8179-8187, 1995.
Kwon et al., *Mol. Biol. of the Cell*, 11:1433-1443, 2000.
McDonnell et al., *J. Bio. Chem.*, 271(14):7891-7894, 1996.
Michalak et al., *Biochem. J.*, 285:681-692, 1992.
Nash et al., *Mol. & Cell. Biochem.*, 135:71-78, 1994.
Pike et al., *Chemical Abstracts*, 130(14), abstract No. 177891, 1999; & *J. Experimental Medicine*, 188(12):2349-2356, 1998.
Pike et al., *Blood*, 94(7):2461-2468, 1999.
Rokeach et al., *Protein Engineering*, 4(8):981-987, 1997.
Routsias et al., *Clinical and Experimental Immunology*, 91(3):437-441, 1993 (abstract only); Medline abstract No. 93185299, XP002133014.
Sontheimer et al., *J. Invest. Med.*, 43(4):362-370, 1995.
Stuart et al., *Febs Letters*, 397:245-249, 1996.
Tosato et al., "Calreticulin and Tumor Suppression," Chapter 16 in *Calreticulin, 2nd ed.*, edited by Eggleron et al., Plenum Publishing, p. 162-179, 2003.

*Primary Examiner*—Misook Yu
(74) *Attorney, Agent, or Firm*—Klarquist Sparkman, LLP

(57) ABSTRACT

Methods for inhibiting endothelial cell growth and angiogenesis, and suppressing tumor growth using calreticulin, fragments of calreticulin and variants of calreticulin are provided. Such methods are useful for the treatment of cancer and diseases associated with unwanted angiogenesis, for example chronic retinal detachment.

15 Claims, 27 Drawing Sheets

SEQUENCE LISTING

<160> NUMBER OF SEQ ID NOS: 35

<210> SEQ ID NO 1
<211> LENGTH: 1251
<212> TYPE: DNA
<213> ORGANISM: Homo sapiens
<220> FEATURE:
<221> NAME/KEY: CDS
<222> LOCATION: (1)..(1251)

<400> SEQUENCE: 1

```
atg ctg cta tcc gtg ccg ttg ctg ctc ggc ctc ctc ggc ctg gcc gtc       48
Met Leu Leu Ser Val Pro Leu Leu Leu Gly Leu Leu Gly Leu Ala Val
  1               5                  10                  15 gcc gag cct gcc gtc tac ttc aag gag cag ttt ctg gac gga gac ggg       96
Ala Glu Pro Ala Val Tyr Phe Lys Glu Gln Phe Leu Asp Gly Asp Gly
                 20                  25                  30 tgg act tcc cgc tgg atc gaa tcc aaa cac aag tca gat ttt ggc aaa      144
Trp Thr Ser Arg Trp Ile Glu Ser Lys His Lys Ser Asp Phe Gly Lys
             35                  40                  45 ttc gtt ctc agt tcc ggc aag ttc tac ggt gac gag gag aaa gat aaa      192
Phe Val Leu Ser Ser Gly Lys Phe Tyr Gly Asp Glu Glu Lys Asp Lys
         50                  55                  60 ggt ttg cag aca agc cag gat gca cgc ttt tat gct ctg tcg gcc agt      240
Gly Leu Gln Thr Ser Gln Asp Ala Arg Phe Tyr Ala Leu Ser Ala Ser
 65                  70                  75                  80 ttc gag cct ttc agc aac aaa ggc cag acg ctg gtg gtg cag ttc acg      288
Phe Glu Pro Phe Ser Asn Lys Gly Gln Thr Leu Val Val Gln Phe Thr
                 85                  90                  95 gtg aaa cat gag cag aac atc gac tgt ggg ggc ggc tat gtg aag ctg      336
Val Lys His Glu Gln Asn Ile Asp Cys Gly Gly Gly Tyr Val Lys Leu
                100                 105                 110 ttt cct aat agt ttg gac cag aca gac atg cac gga gac tca gaa tac      384
Phe Pro Asn Ser Leu Asp Gln Thr Asp Met His Gly Asp Ser Glu Tyr
```

-continued

```
            115                 120                 125
aac atc atg ttt ggt ccc gac atc tgt ggc cct ggc acc aag aag gtt        432
Asn Ile Met Phe Gly Pro Asp Ile Cys Gly Pro Gly Thr Lys Lys Val
130                 135                 140 cat gtc atc ttc aac tac aag ggc aag aac gtg ctg atc aac aag gac        480
His Val Ile Phe Asn Tyr Lys Gly Lys Asn Val Leu Ile Asn Lys Asp
145                 150                 155                 160 atc cgt tgc aag gat gat gag ttt aca cac ctg tac aca ctg att gtg        528
Ile Arg Cys Lys Asp Asp Glu Phe Thr His Leu Tyr Thr Leu Ile Val
                165                 170                 175 cgg cca gac aac acc tat gag gtg aag att gac aac agc cag gtg gag        576
Arg Pro Asp Asn Thr Tyr Glu Val Lys Ile Asp Asn Ser Gln Val Glu
            180                 185                 190 tcc ggc tcc ttg gaa gac gat tgg gac ttc ctg cca ccc aag aag ata        624
Ser Gly Ser Leu Glu Asp Asp Trp Asp Phe Leu Pro Pro Lys Lys Ile
        195                 200                 205 aag gat cct gat gct tca aaa ccg gaa gac tgg gat gag cgg gcc aag        672
Lys Asp Pro Asp Ala Ser Lys Pro Glu Asp Trp Asp Glu Arg Ala Lys
210                 215                 220 atc gat gat ccc aca gac tcc aag cct gag gac tgg gac aag ccc gag        720
Ile Asp Asp Pro Thr Asp Ser Lys Pro Glu Asp Trp Asp Lys Pro Glu
225                 230                 235                 240 cat atc cct gac cct gat gct aag aag ccc gag gac tgg gat gaa gag        768
His Ile Pro Asp Pro Asp Ala Lys Lys Pro Glu Asp Trp Asp Glu Glu
                245                 250                 255 atg gac gga gag tgg gaa ccc cca gtg att cag aac cct gag tac aag        816
Met Asp Gly Glu Trp Glu Pro Pro Val Ile Gln Asn Pro Glu Tyr Lys
            260                 265                 270 ggt gag tgg aag ccc cgg cag atc gac aac cca gat tac aag ggc act        864
Gly Glu Trp Lys Pro Arg Gln Ile Asp Asn Pro Asp Tyr Lys Gly Thr
        275                 280                 285 tgg atc cac cca gaa att gac aac ccc gag tat tct ccc gat ccc agt        912
Trp Ile His Pro Glu Ile Asp Asn Pro Glu Tyr Ser Pro Asp Pro Ser
290                 295                 300 atc tat gcc tat gat aac ttt ggc gtg ctg ggc ctg gac ctc tgg cag        960
Ile Tyr Ala Tyr Asp Asn Phe Gly Val Leu Gly Leu Asp Leu Trp Gln
305                 310                 315                 320 gtc aag tct ggc acc atc ttt gac aac ttc ctc atc acc aac gat gag       1008
Val Lys Ser Gly Thr Ile Phe Asp Asn Phe Leu Ile Thr Asn Asp Glu
                325                 330                 335 gca tac gct gag gag ttt ggc aac gag acg tgg ggc gta aca aag gca       1056
Ala Tyr Ala Glu Glu Phe Gly Asn Glu Thr Trp Gly Val Thr Lys Ala
            340                 345                 350 gca gag aaa caa atg aag gac aaa cag gac gag gag cag agg ctt aag       1104
Ala Glu Lys Gln Met Lys Asp Lys Gln Asp Glu Glu Gln Arg Leu Lys
        355                 360                 365 gag gag gaa gaa gac aag aaa cgc aaa gag gag gag gca gag gac           1152
Glu Glu Glu Glu Asp Lys Lys Arg Lys Glu Glu Glu Ala Glu Asp
370                 375                 380 aag gag gat gat gag gac aaa gat gag gat gag gag gat gag gag gac       1200
Lys Glu Asp Asp Glu Asp Lys Asp Glu Asp Glu Glu Asp Glu Glu Asp
385                 390                 395                 400 aag gag gaa gat gag gag gaa gat gtc ccc ggc cag gcc aag gac gag       1248
Lys Glu Glu Asp Glu Glu Glu Asp Val Pro Gly Gln Ala Lys Asp Glu
                405                 410                 415 ctg                                                                    1251
Leu

<210> SEQ ID NO 2
```

```
<211> LENGTH: 417
<212> TYPE: PRT
<213> ORGANISM: Homo sapiens

<400> SEQUENCE: 2

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Glu Asp Lys Asp Glu Asp Glu Glu Asp Glu Glu Asp
```

```
                385                 390                 395                 400
Lys Glu Glu Asp Glu Glu Asp Val Pro Gly Gln Ala Lys Asp Glu
            405                 410                 415

Leu

<210> SEQ ID NO 3
<211> LENGTH: 400
<212> TYPE: PRT
<213> ORGANISM: Homo sapiens

<400> SEQUENCE: 3

Glu Pro Ala Val Tyr Phe Lys Glu Gln Phe Leu Asp Gly Asp Gly Trp
 1               5                  10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
```

-continued

```
                340                 345                 350
Glu Glu Glu Asp Lys Lys Arg Lys Glu Glu Glu Ala Glu Asp Lys
            355                 360                 365
Glu Asp Asp Glu Asp Lys Asp Glu Asp Glu Glu Asp Glu Glu Asp Lys
        370                 375                 380
Glu Glu Asp Glu Glu Asp Val Pro Gly Gln Ala Lys Asp Glu Leu
385                 390                 395                 400

<210> SEQ ID NO 4
<211> LENGTH: 180
<212> TYPE: PRT
<213> ORGANISM: Homo sapiens

<400> SEQUENCE: 4

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu
            180

<210> SEQ ID NO 5
<211> LENGTH: 61
<212> TYPE: PRT
<213> ORGANISM: Homo sapiens

<400> SEQUENCE: 5

Cys Gly Pro Gly Thr Lys Lys Val His Val Ile Phe Asn Tyr Lys Gly
1               5                   10                  15

Lys Asn Val Leu Ile Asn Lys Asp Ile Arg Cys Lys Asp Asp Glu Phe
            20                  25                  30

Thr His Leu Tyr Thr Leu Ile Val Arg Pro Asp Asn Thr Tyr Glu Val
        35                  40                  45

Lys Ile Asp Asn Ser Gln Val Glu Ser Gly Ser Leu Glu
    50                  55                  60

<210> SEQ ID NO 6
<211> LENGTH: 49
<212> TYPE: PRT
```

```
<213> ORGANISM: Homo sapiens

<400> SEQUENCE: 6

Asn Tyr Lys Gly Lys Asn Val Leu Ile Asn Lys Asp Ile Arg Cys Lys
 1               5                  10                  15

Asp Asp Glu Phe Thr His Leu Tyr Thr Leu Ile Val Arg Pro Asp Asn
             20                  25                  30

Thr Tyr Glu Val Lys Ile Asp Asn Ser Gln Val Glu Ser Gly Ser Leu
         35                  40                  45

Glu

<210> SEQ ID NO 7
<211> LENGTH: 1958
<212> TYPE: DNA
<213> ORGANISM: Homo sapiens
<220> FEATURE:
<221> NAME/KEY: CDS
<222> LOCATION: (109)..(1362)

<400> SEQUENCE: 7
gaattccgga tcatcttaac ctcctccccc cccccccccg tccgtactgc agagccgctg     60
ccggagggtc gttttaaagg gccgcgcgtt gccgccccct cggccgcc atg ctg cta    117
                                                     Met Leu Leu
                                                       1 tcc gtg ccg ttg ctg ctc ggc ctc ctc ggc ctg gcc gtc gcc gag cct    165
Ser Val Pro Leu Leu Leu Gly Leu Leu Gly Leu Ala Val Ala Glu Pro
     5                  10                  15 gcc gtc tac ttc aag gag cag ttt ctg gac gga gac ggg tgg act tcc    213
Ala Val Tyr Phe Lys Glu Gln Phe Leu Asp Gly Asp Gly Trp Thr Ser
 20                  25                  30                  35 cgc tgg atc gaa tcc aaa cac aag tca gat ttt ggc aaa ttc gtt ctc    261
Arg Trp Ile Glu Ser Lys His Lys Ser Asp Phe Gly Lys Phe Val Leu
                 40                  45                  50 agt tcc ggc aag ttc tac ggt gac gag gag aaa gat aaa ggt ttg cag    309
Ser Ser Gly Lys Phe Tyr Gly Asp Glu Glu Lys Asp Lys Gly Leu Gln
             55                  60                  65 aca agc cag gat gca cgc ttt tat gct ctg tcg gcc agt ttc gag cct    357
Thr Ser Gln Asp Ala Arg Phe Tyr Ala Leu Ser Ala Ser Phe Glu Pro
         70                  75                  80 ttc agc aac aaa ggc cag acg ctg gtg gtg cag ttc acg gtg aaa cat    405
Phe Ser Asn Lys Gly Gln Thr Leu Val Val Gln Phe Thr Val Lys His
 85                  90                  95 gag cag aac atc gac tgt ggg ggc ggc tat gtg aag ctg ttt cct aat    453
Glu Gln Asn Ile Asp Cys Gly Gly Gly Tyr Val Lys Leu Phe Pro Asn
100                 105                 110                 115 agt ttg gac cag aca gac atg cac gga gac tca gaa tac aac atc atg    501
Ser Leu Asp Gln Thr Asp Met His Gly Asp Ser Glu Tyr Asn Ile Met
                 120                 125                 130 ttt ggt ccc gac atc tgt ggc cct ggc acc aag aag gtt cat gtc atc    549
Phe Gly Pro Asp Ile Cys Gly Pro Gly Thr Lys Lys Val His Val Ile
             135                 140                 145 ttc aac tac aag ggc aag aac gtg ctg atc aac aag gac atc cgt tgc    597
Phe Asn Tyr Lys Gly Lys Asn Val Leu Ile Asn Lys Asp Ile Arg Cys
         150                 155                 160 aag gat gat gag ttt aca cac ctg tac aca ctg att gtg cgg cca gac    645
Lys Asp Asp Glu Phe Thr His Leu Tyr Thr Leu Ile Val Arg Pro Asp
     165                 170                 175 aac acc tat gag gtg aag att gac aac agc cag gtg gag tcc ggc tcc    693
Asn Thr Tyr Glu Val Lys Ile Asp Asn Ser Gln Val Glu Ser Gly Ser
180                 185                 190                 195
```

```
ttg gaa gac gat tgg gac ttc ctg cca ccc aag aag ata aag gat cct     741
Leu Glu Asp Asp Trp Asp Phe Leu Pro Pro Lys Lys Ile Lys Asp Pro
            200                 205                 210 gat gct tca aaa ccg gaa gac tgg gat gag cgg gcc aag atc gat gat     789
Asp Ala Ser Lys Pro Glu Asp Trp Asp Glu Arg Ala Lys Ile Asp Asp
            215                 220                 225 ccc aca gac tcc aag cct gag gac tgg gac aag ccc gag cat atc cct     837
Pro Thr Asp Ser Lys Pro Glu Asp Trp Asp Lys Pro Glu His Ile Pro
            230                 235                 240 gac cct gat gct aag aag ccc gag gac tgg gat gaa gag atg gac gga     885
Asp Pro Asp Ala Lys Lys Pro Glu Asp Trp Asp Glu Glu Met Asp Gly
        245                 250                 255 gag tgg gaa ccc cca gtg att cag aac cct gag tac aag ggt gag tgg     933
Glu Trp Glu Pro Pro Val Ile Gln Asn Pro Glu Tyr Lys Gly Glu Trp
260                 265                 270                 275 aag ccc cgg cag atc gac aac cca gat tac aag ggc act tgg atc cac     981
Lys Pro Arg Gln Ile Asp Asn Pro Asp Tyr Lys Gly Thr Trp Ile His
                280                 285                 290 cca gaa att gac aac ccc gag tat tct ccc gat ccc agt atc tat gcc    1029
Pro Glu Ile Asp Asn Pro Glu Tyr Ser Pro Asp Pro Ser Ile Tyr Ala
            295                 300                 305 tat gat aac ttt ggc gtg ctg ggc ctg gac ctc tgg cag gtc aag tct    1077
Tyr Asp Asn Phe Gly Val Leu Gly Leu Asp Leu Trp Gln Val Lys Ser
            310                 315                 320 ggc acc atc ttt gac aac ttc ctc atc acc aac gat gag gca tac gct    1125
Gly Thr Ile Phe Asp Asn Phe Leu Ile Thr Asn Asp Glu Ala Tyr Ala
        325                 330                 335 gag gag ttt ggc aac gag acg tgg ggc gta aca aag gca gca gag aaa    1173
Glu Glu Phe Gly Asn Glu Thr Trp Gly Val Thr Lys Ala Ala Glu Lys
340                 345                 350                 355 caa atg aag gac aaa cag gac gag gag cag agg ctt aag gag gag gaa    1221
Gln Met Lys Asp Lys Gln Asp Glu Glu Gln Arg Leu Lys Glu Glu Glu
                360                 365                 370 gaa gac aag aaa cgc aaa gag gag gag gag gca gag gac aag gag gat    1269
Glu Asp Lys Lys Arg Lys Glu Glu Glu Glu Ala Glu Asp Lys Glu Asp
            375                 380                 385 gat gag gac aaa gat gag gat gag gag gat gag gag gac aag gag gaa    1317
Asp Glu Asp Lys Asp Glu Asp Glu Glu Asp Glu Glu Asp Lys Glu Glu
        390                 395                 400 gat gag gag gaa gat gtc ccc ggc cag gcc aag gac gag ctg tag        1362
Asp Glu Glu Glu Asp Val Pro Gly Gln Ala Lys Asp Glu Leu
        405                 410                 415 agaggcctgc ctccagggct ggactgaggc ctgagcgctc ctgccgcaga gcttgccgcg   1422
ccaaataatg tctctgtgag actcgagaac tttcattttt ttccaggctg gttcggattt   1482
ggggtggatt ttggttttgt tccctcctc cactctcccc caccccctcc ccgccttttt    1542
tttttatttt tttaaactgg tattttatct ttgattctcc ttcagccctc accctggtt    1602 ctcatctttc ttgatcaaca tcttttcttg cctctgtccc cttctctcat ctcttagctc   1662
ccctccaacc tgggggcag tggtgtggag aagccacagg cctgagattt catctgctct    1722
ccttcctgga gcccagagga gggcagcaga aggggtggt gtctccaacc ccccagcact    1782
gaggaagaac ggggctcttc tcatttcacc cctccctttc tccctgcccc caggactgg    1842 gccacttctg ggtgggcag tgggtcccag attggctcac actgagaatg taagaactac    1902
aaacaaaatt tctattaaat taaattttgt gtctcaaaaa aaaaaaaag gaattc         1958

<210> SEQ ID NO 8
```

```
<211> LENGTH: 60
<212> TYPE: PRT
<213> ORGANISM: Homo sapiens

<400> SEQUENCE: 8

Gly Pro Gly Thr Lys Lys Val His Val Ile Phe Asn Tyr Lys Gly Lys
  1               5                  10                  15

Asn Val Leu Ile Asn Lys Asp Ile Arg Cys Lys Asp Asp Glu Phe Thr
             20                  25                  30

His Leu Tyr Thr Leu Ile Val Arg Pro Asp Asn Thr Tyr Glu Val Lys
         35                  40                  45

Ile Asp Asn Ser Gln Val Glu Ser Gly Ser Leu Glu
 50                  55                  60

<210> SEQ ID NO 9
<211> LENGTH: 280
<212> TYPE: PRT
<213> ORGANISM: Homo sapiens

<400> SEQUENCE: 9

Gly Pro Gly Thr Lys Lys Val His Val Ile Phe Asn Tyr Lys Gly Lys
  1               5                  10                  15

Asn Val Leu Ile Asn Lys Asp Ile Arg Cys Lys Asp Asp Glu Phe Thr
             20                  25                  30

His Leu Tyr Thr Leu Ile Val Arg Pro Asp Asn Thr Tyr Glu Val Lys
         35                  40                  45

Ile Asp Asn Ser Gln Val Glu Ser Gly Ser Leu Glu Asp Trp Asp
 50                  55                  60

Phe Leu Pro Pro Lys Lys Ile Lys Asp Pro Asp Ala Ser Lys Pro Glu
 65                  70                  75                  80

Asp Trp Asp Glu Arg Ala Lys Ile Asp Asp Pro Thr Asp Ser Lys Pro
                 85                  90                  95

Glu Asp Trp Asp Lys Pro Glu His Ile Pro Asp Pro Asp Ala Lys Lys
                100                 105                 110

Pro Glu Asp Trp Asp Glu Glu Met Asp Gly Glu Trp Glu Pro Pro Val
                115                 120                 125

Ile Gln Asn Pro Glu Tyr Lys Gly Glu Trp Lys Pro Arg Gln Ile Asp
            130                 135                 140

Asn Pro Asp Tyr Lys Gly Thr Trp Ile His Pro Glu Ile Asp Asn Pro
145                 150                 155                 160

Glu Tyr Ser Pro Asp Pro Ser Ile Tyr Ala Tyr Asp Asn Phe Gly Val
                165                 170                 175

Leu Gly Leu Asp Leu Trp Gln Val Lys Ser Gly Thr Ile Phe Asp Asn
                180                 185                 190

Phe Leu Ile Thr Asn Asp Glu Ala Tyr Ala Glu Glu Phe Gly Asn Glu
            195                 200                 205

Thr Trp Gly Val Thr Lys Ala Ala Glu Lys Gln Met Lys Asp Lys Gln
            210                 215                 220

Asp Glu Glu Gln Arg Leu Lys Glu Glu Glu Asp Lys Lys Arg Lys
225                 230                 235                 240

Glu Glu Glu Glu Ala Glu Asp Lys Glu Asp Asp Glu Asp Lys Asp Glu
                245                 250                 255

Asp Glu Glu Asp Glu Glu Asp Lys Glu Glu Asp Glu Glu Glu Asp Val
                260                 265                 270

Pro Gly Gln Ala Lys Asp Glu Leu
                275                 280
```

```
<210> SEQ ID NO 10
<211> LENGTH: 7
<212> TYPE: PRT
<213> ORGANISM: Artificial Sequence
<220> FEATURE:
<221> NAME/KEY: Variable
<222> LOCATION: 2
<223> OTHER INFORMATION: Xaa represents I, L, G, C, or A
<220> FEATURE:
<223> OTHER INFORMATION: Description of Artificial Sequence:Consensus
      integrin sequence

<400> SEQUENCE: 10

Lys Xaa Gly Phe Phe Lys Arg
  1               5

<210> SEQ ID NO 11
<211> LENGTH: 6
<212> TYPE: PRT
<213> ORGANISM: Artificial Sequence
<220> FEATURE:
<221> NAME/KEY: Variable
<222> LOCATION: 2
<223> OTHER INFORMATION: Xaa represents G, V, or A
<220> FEATURE:
<221> NAME/KEY: Variable
<222> LOCATION: 5
<223> OTHER INFORMATION: Xaa represents K or R
<220> FEATURE:
<223> OTHER INFORMATION: Description of Artificial Sequence:Consensus
      steroid nuclear receptor sequence

<400> SEQUENCE: 11

Lys Xaa Phe Phe Xaa Arg
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 12

Lys Ile Gly Phe Phe Lys Arg
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 13

Lys Leu Gly Phe Phe Lys Arg
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 14
```

```
Lys Gly Gly Phe Phe Lys Arg
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 15

Lys Ala Gly Phe Phe Lys Arg
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 16

Lys Cys Gly Phe Phe Lys Arg
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 17

Lys Cys Gly Phe Phe Asp Arg
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 18

Arg Met Gly Phe Phe Lys Arg
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:Portion of
      integrin sequence

<400> SEQUENCE: 19

Lys Val Gly Phe Phe Lys Arg
 1               5

<210> SEQ ID NO 20
<211> LENGTH: 7
<212> TYPE: PRT
<213> ORGANISM: Artificial Sequence
```

```
<220> FEATURE:
<223> OTHER INFORMATION: Description of Artificial Sequence:Portion of
      integrin sequence

<400> SEQUENCE: 20

Lys Cys Gly Phe Phe Asn Arg
1               5

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 21

Ala Cys Glu Gly Cys Lys Gly Phe Phe Arg Arg Ser Val Gln Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 22

Thr Cys Glu Gly Cys Lys Gly Phe Phe Arg Arg Thr Ile Gln Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 23

Thr Cys Glu Gly Cys Lys Gly Phe Phe Arg Arg Ser Met Lys Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 24

Thr Cys Gly Ser Cys Lys Val Phe Phe Lys Arg Ala Val Glu Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 25
```

Thr Cys Gly Ser Cys Lys Val Phe Phe Lys Arg Ala Ala Glu Lys
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 26

Thr Cys Gly Ser Cys Lys Val Phe Phe Lys Arg Ala Met Glu Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 27

Ser Cys Glu Gly Cys Lys Ala Phe Phe Lys Arg Ser Ile Gln Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 28

Ser Cys Glu Gly Cys Lys Gly Phe Phe Lys Arg Thr Val Arg Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 29

Thr Cys Glu Gly Cys Thr Gly Phe Phe Lys Arg Ser Ile Arg Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:Portion of
      steroid nuclear receptor

<400> SEQUENCE: 30

Thr Cys Glu Gly Cys Lys Gly Phe Phe Lys Arg Thr Val Gln Lys
1               5                   10                  15

<210> SEQ ID NO 31
<211> LENGTH: 15
<212> TYPE: PRT
<213> ORGANISM: Artificial Sequence

```
<220> FEATURE:
<223> OTHER INFORMATION: Description of Artificial Sequence:Portion of
      steroid nuclear receptor

<400> SEQUENCE: 31

Ser Cys Glu Gly Cys Lys Gly Phe Phe Lys Arg Thr Val Arg Lys
 1               5                  10                  15

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence:Portion of
      glucocorticoid receptor

<400> SEQUENCE: 32

Lys Val Phe Phe Lys Arg
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:Portion of
      estrogen receptor

<400> SEQUENCE: 33

Lys Ala Phe Phe Lys Arg
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:Portion of
      thyroid receptor

<400> SEQUENCE: 34

Lys Ser Phe Phe Arg Arg
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:Portion of
      retinoic acid receptor

<400> SEQUENCE: 35

Lys Gly Phe Phe Arg Arg
 1               5
```

USE OF CALRETICULIN AND CALRETICULIN FRAGMENTS TO INHIBIT ENDOTHELIAL CELL GROWTH AND ANGIOGENESIS, AND SUPPRESS TUMOR GROWTH

CROSS REFERENCE TO RELATED APPLICATIONS

This is a divisional of U.S. patent application Ser. No. 09/807,148, filed Apr. 5, 2001 now U.S. Pat. No. 6,867,180, which is the § 371 U.S. National Phase of International Application No. PCT/US99/23240, filed Oct. 5, 1999, which was published in English under PCT Article 21(2), which in turn claims the benefit of U.S. Provisional Application No. 60/103,438, filed Oct. 6, 1998, all of which are incorporated herein by reference.

FIELD OF THE INVENTION

This invention relates to inhibition of endothelial cell growth, angiogenesis and tumor growth.

BACKGROUND OF THE INVENTION

A. Tumor Growth and Invasion

Tumor growth and invasion into normal tissues is dependent upon an adequate blood supply (Folkman, *Ann. N.Y. Acad. Sci.* 401:212-227, 1982; Kerbel, *Bioessays* 13:31-36, 1991). Agents that target tumor blood supply have been shown to prevent or delay tumor formation, and to promote the regression or dormancy of established tumors in preclinical models. Thus, antibodies against the endothelial cell growth factor VEGF (vascular endothelial growth factor), which is produced at high levels by various types of tumors (Dvorak et al., *J. Exp. Med.* 174:1275-1278, 1991), antibodies to VEGF receptor 2, and soluble VEGF receptors all have been shown to reduce tumor growth in experimental animal models (Kendall and Thomas, *Proc. Natl. Acad. Sci. U.S.A.* 90:10705-10709, 1993; Kim et al., *Nature* 362:841-844, 1993; Skobe et al., *Nat Med.* 3:1222-1227, 1997). Antibodies to the integrin $\alpha_v\beta_3$, which is expressed at high levels by angiogenic blood vessels and permits endothelial cells to interact with components of the extracellular matrix, have been shown to disrupt ongoing angiogenesis on the chick chorioallantoid membrane and produce regression of human tumors transplanted into this site (Cheresh and Spiro, *J. Biol. Chem.* 262:17703-17711, 1987; Brooks et al., *Cell* 79:1157-1164, 1994).

A truncated form of tissue factor targeted to tumor vascular endothelium was demonstrated to initiate formation of intravascular clots and promote the regression of experimental tumors established in mice (Huang et al., *Science* 275:547-550, 1997). Angiostatin, a fragment of plasminogen (O'Reilly et al., *Cell* 79:315-328, 1994), and endostatin, a fragment of collagen XVIII (O'Reilly et al., *Cell* 88:277-285, 1997), are known to inhibit the proliferation of endothelial cells in vitro and to suppress neovascularization in vivo. Both compounds also inhibit the growth of a variety of tumors in mice, and upon repeated cycles of treatment, promote sustained tumor dormancy without inducing drug resistance (O'Reilly et al., *Nat. Med.* 2:689-692, 1996; Boehm et al., *Nature* 390:404-407, 1997).

Other multifunctional drugs that can also inhibit angiogenesis have displayed antitumor effects. These include Interleukin-12 (Voest et al., *J. Natl. Cancer Inst.* 87:581-586, 1995) the Interferon-γ Inducible Protein-10 (Angiolillo et al., *J. Exp. Med.* 182:155-162, 1995; Strieter et al., *Biochem. Biophys. Res. Commun.* 210:51-57, 1995; Sgadari et al., *Proc. Natl. Acad. Sci. U.S.A.* 93:13791-13796, 1996), the monokine induced by Interferon-γ (Sgadari et al., *Blood* 89:2635-2643, 1997), a fragment of prolactin (Clapp et al., *Endocrinology* 133:1292-1299, 1993), synthetic analogues of fumagillin (Ingber et al., *Nature* 348:555-557, 1990), thalidomide (D'Amato et al., *Proc Natl Acad Sci U.S.A.* 91:4082-4085, 1994), Platelet Factor-4 (Maione et al., *Science* 247:77-79, 1990), and thrombospondin (Good et al., *Proc Natl Acad Sci U.S.A.* 87:6624-6628, 1990; Weinstat-Saslow et al., *Cancer Res.* 54:6504-6511, 1994).

B. Calreticulin

Calreticulin was first identified in skeletal muscle sarcoplasmic reticulum. (Ostwald and MacLennan, *J. Biol. Chem.* 249 (3):974-979, 1974). Fifteen years later it was cloned and the N-terminus was sequenced. This led to the discovery that several groups had independently identified the molecule and had given it different names, including, "high-affinity $Ca^{2+}$", "calregulin", "CRP55" and "calsequestrin-like protein" (Ostwald and MacLennan, *J. Biol. Chem.* 249 (3):974-979, 1974; Waisman et al., *J. Biol. Chem.* 260(3):1652-1660, 1985; Macer, D. R. J. & Koch, G. L. E. *J. Cell. Sci.* 91:61-70, 1988; Damiani et al., *Biochem Biophys Res Commun* 165(3):973-980, 1989; Treves et al., *Biochem. J.* 271:473-480, 1990). Each of these groups identified calreticulin through different means, but all identified its ability to bind $Ca^{2+}$.

Although most studies have indicated that calreticulin resides predominantly within the lumen of the endoplasmic reticulum, calreticulin may also be found in other cellular compartments. For example, calreticulin was detected on the plasma membranes of lymphoblastoid cells (Newkirk and Tsoukas, *J. Autoimmun.* 5:511-525, 1992) and epidermal keratinocyte lines (Kawashima, et al., *Dermatology* 189 Suppl. 1:6-10, 1994). It was proposed to represent, or to be closely related in structure, to the C1q receptor found on endothelial cells, B cells, T cells and other cells (Chen et al., *J. Immunol.* 153:1430-1440, 1994). Calreticulin is also a constituent of lytic granules contained in cytotoxic T and NK cells from which it is released during cell lysis (Dupuis et al., *J. Exp. Med.* 177:1-7, 1993), and has been purified from the culture supernatant of several cell types (Booth and Koch, *Cell* 59:729-737, 1989; Eggleton et al., *Clin. Immunol. Immunopathol.* 72:405-409, 1994) and from normal human plasma (Sueyoshi et al., *Thromb. Res.* 63:569-575, 1991). Several observations support the notion that calreticulin can also be a target for autoimmune responses (Lux et al., *J. Clin. Invest.* 89:1945-1951, 1992; Meilof et al., *J. Immunol.* 151:5800-5809, 1993).

Since the initial identification and cloning, the structure of calreticulin has been characterized. Mammalian calreticulin is a 417 amino acid peptide from which the 17 N-terminal amino acids are cleaved upon translocation to the lumen of the endoplasmic reticulum (Smith and Koch, *Embo. J* 8(12):3581-3586, 1989). In addition to being found in the lumen of the endoplasmic reticulum, calreticulin has been found in the cytoplasm, in the nucleus of some cells, and in the extracellular matrix (Michalak et al., *Biochem. J.* 285:681-692, 1992). Further studies revealed that calreticulin has three distinct domains, the N-terminal domain, a middle domain and the C-terminal domain.

The mature calreticulin is composed of an N-terminal domain consisting of 180 amino acids that are highly conserved. Proposed three-dimensional models indicate that the domain contains eight anti-parallel β-strands. Furthermore, the N-terminal domain has been found to bind a number of molecules including the alpha subunit of integrin, $Zn^{2+}$, and the DNA binding domain of steroid receptors (Nash et al., *Mol. Cellular Biochem.* 135:71-78, 1994).

The middle domain of calreticulin stretches from amino acid 180 to amino acid 280. It is proline rich and has also been termed the P-domain. This domain has been found to have a high affinity for $Ca^{2+}$ and contains a nuclear localization signal (Baksh and Michalak, *J. Biol. Chem.* 266:21458-21465, 1991).

Following the P-domain is the C-domain. This last domain is highly acidic and contains an endoplasmic reticulum retention signal. The C-domain binds to Factor IX, Factor X, and prothrombin (See U.S. Pat. No. 5,426,097, to Stern et al.).

Calreticulin has also been found to be useful in wound healing (See U.S. Pat. No. 5,591,716, to Siebert et al.).

SUMMARY

Calreticulin has been actively studied since 1972. Some of the studies that have been done have focused on understanding the structure of calreticulin while others have focused on understanding the physiological role of the molecule.

The present invention stems from the discovery that calreticulin has three previously uncharacterized biological activities. First, calreticulin is shown to inhibit endothelial cell growth, while having little or no effect on the growth of non-endothelial cells. Second, calreticulin is shown to inhibit angiogenesis. Third, calreticulin is shown to inhibit tumor growth, including the growth of Burkitt lymphoma, breast adenocarcinomas, colon carcinomas, lung carcinomas, melanoma, rhabdomyosarcoma, promyelomonocytic lymphoma, Wilms tumor, and neuroblastoma tumors.

It has also been discovered that certain fragments of calreticulin share these activities. These fragments include calreticulin lacking the N-terminal 1-120 amino acids (Seq. I.D. No. 9), the N-terminal domain (Seq. I.D. No. 4), as well as, fragments of the N-terminal domain of calreticulin. Examples of these fragments include the recombinantly produced 180 amino acid N-terminal domain of calreticulin (Seq. I.D. No. 4), which has been given the name "vasostatin", Δ120 calreticulin (calreticulin missing the N-terminal 1-120 amino acids; Seq. I.D. No. 9), as well as a recombinantly produced 61 amino acid fragment (a.a. 120-180; Seq. I.D. No. 5). Other biologically active fragments of calreticulin include a synthetic 49 amino acid fragment (a.a. 132-180; Seq. I.D. No. 6) and a synthetic 60 amino acid fragment (a.a. 121-180; Seq. I.D. No. 8).

Additionally, the activity of the above described molecules does not stem from their ability to bind to the sequence $KXaa_1FFXaa_2R$ (Seq. I.D. No. 11; $Xaa_1$ represents either G, A, or V, and $Xaa_2$ represents K or R) or the sequence $KXaa_1GFFKR$ (Seq. I.D. No. 10; $Xaa_1$ represents either I, L, G, A, or C) that are known to bind calreticulin.

Calreticulin and the described fragments of calreticulin are useful among other things for inhibiting endothelial cell growth, for the treatment of subjects having solid tumors with associated neovascularization, and for the treatment of other diseases where angiogenesis is a factor. In particular, the present invention may be especially useful for treating rheumatoid arthritis, autoimmune diseases, rheumatic diseases, and certain ocular neovascular diseases, such as, macular degeneration, diabetic retinopathy, and retrolental fibroplasia.

Pharmaceutical compositions comprising calreticulin and the therapeutically active fragments and variants of calreticulin are provided by the invention. In particular embodiments, the biologically active fragments are those fragments having the sequences shown in Seq. I.D. Nos. 4, 5, 6, 8, and 9.

In other aspects, the invention provides a method of inhibiting endothelial cell growth by contacting endothelial cells with a pharmaceutical composition that comprises at least one protein selected from the group consisting of calreticulin, and therapeutically effective fragments of calreticulin. The invention also provides a method of inhibiting angiogenesis in a subject, by administering to the subject an effective amount of a pharmaceutical composition comprising at least one protein selected from the group consisting of calreticulin and therapeutically effective fragments and variants of calreticulin.

With respect to the anti-tumor activities of the molecules provided, another aspect of the invention is a method of inhibiting tumor angiogenesis and growth by contacting tumor cells with an effective amount of a pharmaceutical composition comprising at least one protein selected from the group consisting of calreticulin and therapeutically effective fragments and variants of calreticulin. The anti-tumor activity may also be utilized in a method of inhibiting tumor growth in a subject. That method comprises administering to the subject an effective amount of a pharmaceutical composition comprising at least one protein selected from the group consisting of calreticulin and therapeutically effective fragments and variants of calreticulin.

Among the compositions provided by the invention is a protein with an amino acid sequence selected from the group consisting of therapeutically effective fragments of vasostatin and variants of calreticulin that do not bind to the sequence shown in Seq. I.D. No. 11 and/or Seq. I.D. No. 10, but yet display one of the three biological activities described above.

The invention also provides methods of identifying therapeutically effective variants and fragments of calreticulin. These methods involve contacting a sample suspected of containing therapeutically effective variants or fragments with the sequence $KXaa_1FFXaa_2R$ (Seq. I.D. No. 11), and/or the sequence $KXaa_1GFFKR$ (Seq. I.D. No. 10) detecting the portion of the sample that does not bind to the sequence. The unbound portion of the sample is then tested for one of the three biological activities described above. Accordingly, the invention also provides the therapeutically effective variants and fragments of calreticulin identified by the method, as well as cells containing recombinant nucleic acid molecules that encode the therapeutically effective variants and fragments.

These and other aspects of the invention are explained in more detail in the following sections.

SEQUENCE LISTING

Figure 1:
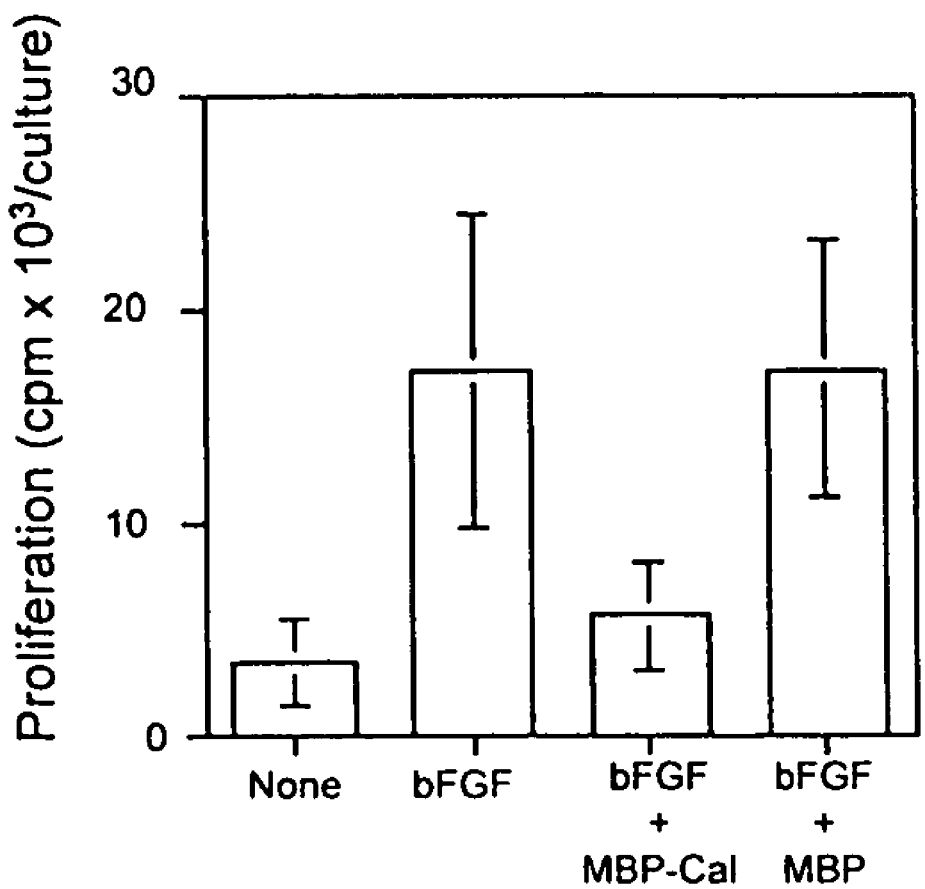
FIG. 1 is a graph showing the inhibition of endothelial cell proliferation by MBP-calreticulin (Seq. I.D. No. 2). Fetal bovine heart endothelial cells (800 cells/well) were incubated for 5 days either in medium alone or medium supplemented with bFGF (25 ng/ml), with or without recombinant purified MBP-calreticulin (Seq. I.D. No. 3) or MBP (both at 1 µg/ml). The results of 16 experiments are expressed as mean cpm (±SD).
Figure 2:
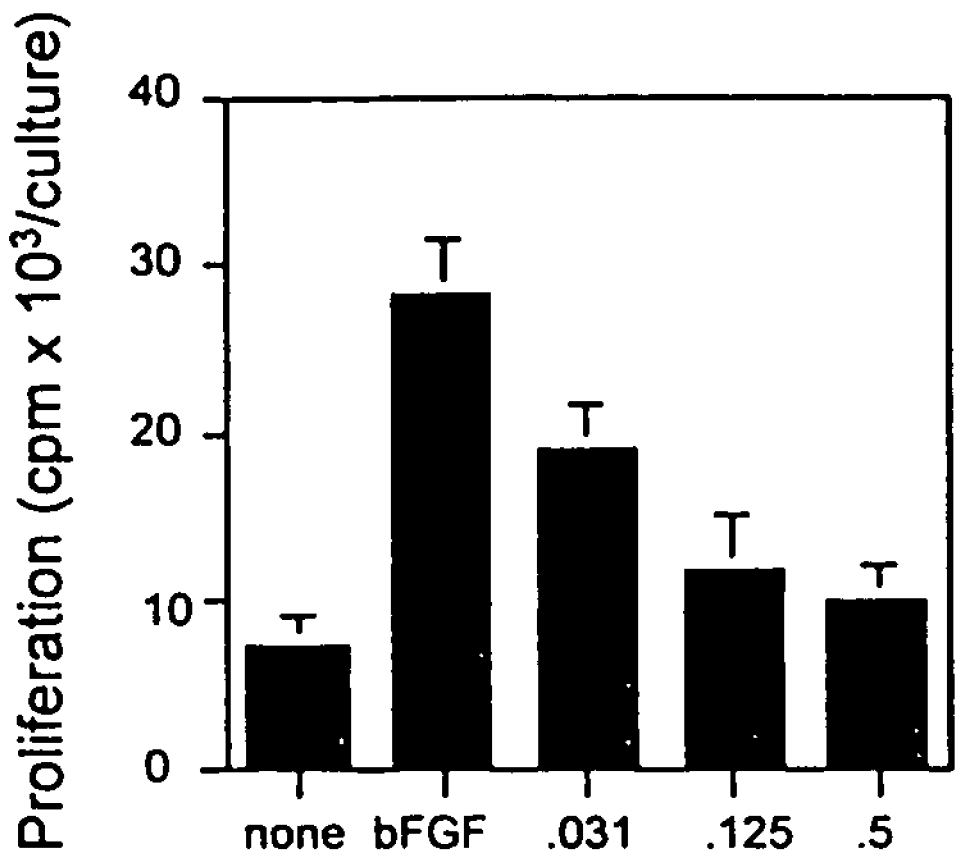
FIG. 2 is a graph showing the dose dependency of MBP-vasostatin (Seq. I.D. No. 4) inhibition.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

Seq. I.D. No. 1 shows the nucleic acid sequence for the open reading frame of human calreticulin.

Seq. I.D. No. 2 shows the amino acid sequence of human calreticulin.

Seq. I.D. No. 3 shows the amino acid sequence of human calreticulin without the 17 N-terminal amino acids (References throughout the text to amino acid numbers are keyed to this sequence).

Seq. I.D. No. 4 shows the amino acid sequence of the N-terminal 180 amino acids of human calreticulin ("vasostatin").

Seq. I.D. No. 5 shows the amino acid sequence of the recombinant 61 amino acid fragment of human calreticulin. This sequence corresponds to amino acids number 120-180 of the human calreticulin sequence.

Seq. I.D. No. 6 shows the amino acid sequence of the synthetic 49 amino acid fragment of human calreticulin. This sequence corresponds to amino acids numbers 132-180 of the human calreticulin sequence.

Seq. I.D. No. 7 shows the cDNA sequence of human calreticulin.

Seq. I.D. No. 8 shows the amino acid sequence of the synthetic 60 amino acid fragment of human calreticulin. This sequence corresponds to amino acids numbers 121-180 of the human calreticulin sequence.

Seq. I.D. No. 9 shows the amino acid sequence of Δ120 calreticulin (calreticulin (Seq. I.D. No. 3) missing the N-terminal 1-120 amino acids).

Seq. I.D. No. 10 shows the integrin consensus amino acid sequence

Seq. I.D. No. 11 shows the steroid nuclear receptor consensus amino acid sequence.

Seq. I.D. No. 12 shows the amino acid sequence of a portion of an integrin.

Seq. I.D. No. 13 shows the amino acid sequence of a portion of an integrin.

Seq. I.D. No. 14 shows the amino acid sequence of a portion of an integrin.

Seq. I.D. No. 15 shows the amino acid sequence of a portion of an integrin.

Seq. I.D. No. 16 shows the amino acid sequence of a portion of an integrin.

Seq. I.D. No. 17 shows the amino acid sequence of a portion of an integrin.

Seq. I.D. No. 18 shows the amino acid sequence of a portion of an integrin.

Seq. I.D. No. 19 shows the amino acid sequence of a portion of an integrin.

Seq. I.D. No. 20 shows the amino acid sequence of a portion of an integrin.

Seq. I.D. No. 21 shows the amino acid sequence of a portion of a steroid nuclear receptor.

Seq. I.D. No. 22 shows the amino acid sequence of a portion of a steroid nuclear receptor.

Seq. I.D. No. 23 shows the amino acid sequence of a portion of a steroid nuclear receptor.

Seq. I.D. No. 24 shows the amino acid sequence of a portion of a steroid nuclear receptor.

Seq. I.D. No. 25 shows the amino acid sequence of a portion of a steroid nuclear receptor.

Seq. I.D. No. 26 shows the amino acid sequence of a portion of a steroid nuclear receptor.

Seq. I.D. No. 27 shows the amino acid sequence of a portion of a steroid nuclear receptor.

Seq. I.D. No. 28 shows the amino acid sequence of a portion of a steroid nuclear receptor.

Seq. I.D. No. 29 shows the amino acid sequence of a portion of a steroid nuclear receptor.

Seq. I.D. No. 30 shows the amino acid sequence of a portion of a steroid nuclear receptor.

Seq. I.D. No. 31 shows the amino acid sequence of a portion of a steroid nuclear receptor.

Seq. I.D. No. 32 shows the amino acid sequence of a portion of the glucocorticoid receptor.

Seq. I.D. No. 33 shows the amino acid sequence of a portion of the estrogen receptor.

Seq. I.D. No. 34 shows the amino acid sequence of a portion of the thyroid receptor.

Seq. I.D. No. 35 shows the amino acid sequence of a portion of the retinoic acid receptor.

DETAILED DESCRIPTION

I. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Calreticulin: Calreticulin is a calcium binding protein that is found in many animals, and is highly conserved across species. The open reading frame of the prototypical human calreticulin is shown in Seq. I.D. No. 1, while the sequence of the human calreticulin protein is shown in Seq. I.D. No. 2. The present invention is founded on the discovery that calreticulin, and particular fragments of calreticulin, possess certain biological activities ("calreticulin activities"). Specifically, these activities include (1) the inhibition of endothelial cell growth; (2) the inhibition of angiogenesis; and (3) the inhibition of tumor growth.

Each of these activities may be separately assayed by methods described herein. The ability of calreticulin or a fragment of this protein to perform these activities may be beneficial in a number of applications, including clinical applications such as tumor therapy and treatment of diseases with abnormal or excessive angiogenesis.

While the amino acid sequence of the prototypical human calreticulin is shown in Seq. I.D. No. 2, one of skill in the art will appreciate that variations in this amino acid sequence (such as amino acid deletions, additions or substitutions) may be made without substantially affecting the activities of the protein (or fragments of the protein) discussed above. Thus, reference herein to the term "calreticulin" encompasses both the protein having the amino acid sequence shown in Seq. I.D. No. 2, as well as amino acid sequences that are based on this sequence but which include one or more sequence variants. Such sequence variants may also be defined in the degree of amino acid sequence identity that they share with the amino acid sequence shown in Seq. I.D. No. 2. Typically, calreticulin sequence variants will share at least 80% sequence identity with the sequence shown in Seq. I.D. No. 2. More highly conserved variants will share at least 90% or at least 95% sequence identity with the Seq. I.D. No. 2 sequence. In addition to sharing sequence identity with the prototypical calreticulin protein sequence, such sequence variants possess at least one of the three biological activities noted above.

Therapeutically effective fragments and variants of calreticulin: It is shown herein that not only does calreticulin possess the specified biological activities (inhibiting endothelial cells, angiogenesis and tumor growth), but that such activities are also found in certain peptide fragments of calreticulin. For example, it is shown that the 180 amino acid N-terminal domain of calreticulin (Seq. I.D. No. 4), which is hereinafter termed "vasostatin," possesses these activities, as do the synthetically produced 49 (Seq. I.D. No. 6) and 60 (Seq. I.D. No. 8) amino acid fragments, as well as the recombinantly produced 61 amino acid fragment (Seq. I.D. No. 5) and Δ120 calreticulin (Seq. I.D. No. 9). Furthermore, it is shown that the activity of these fragments does not stem from their ability to bind to the amino acid sequence motif $KXaa_1FFXaa_2R$ (Seq. I.D. No. 11), that is found in the a family of steroid receptors (glucocorticoid, mineralcorticoid, progesterone and androgen receptors: KVFFKR (Seq. I.D. No. 32); estrogen receptor: KAFFKR (Seq. I.D. No. 33); thyroid hormone receptor: KSFFRR (Seq. I.D. No. 34); and retinoic acid receptor: KGFFRR (Seq. I.D. No. 35).

Furthermore, it is shown that the activity of these fragments does not stem from their ability to bind to the amino acid sequence motif found in the alpha subunit of integrins. The consensus sequence representing the alpha subunit of integrin is $KXaa_1GFFKR$ (Seq. I.D. No. 10).

Hence, the terms "therapeutically effective fragment of calreticulin" or "therapeutically effective variant of calreticulin" includes any calreticulin fragment or variant that, at a minimum, possesses one of the three biological activities noted above. For example, the 61 amino acid calreticulin fragment (Seq. I.D. No. 5) is a therapeutically effective fragment of calreticulin since it possesses the ability to inhibit endothelial cell growth. Whether a given calreticulin fragment or variant possesses one or more of these biological activities can be readily determined by the assays described herein. For example, the ability to inhibit endothelial cell growth can readily be determined for any given fragment of calreticulin using the simple in vitro assay described below.

Oligonucleotide: A linear polynucleotide sequence of up to about 100 nucleotide bases in length.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Sequence identity: the similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of calreticulin will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981); Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.*, 6:119-129, 1994 presents a detailed consideration of sequence alignment methods and homology calculations.

The NCBI Basic Local Alignment Search Tool (BLAST) (Altschul et al., *J. Mol. Biol.*, 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available at the NCBI website.

Homologs and variants of calreticulin are typically characterized by possession of at least 50% sequence identity counted over the full length alignment with the amino acid sequence of calreticulin using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, homologs and variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. One of skill in the art will appreciate that these sequence identity ranges are provided for guidance only; it is entirely possible that strongly significant homologs could be obtained that fall outside of the ranges provided.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Subject: Living multi-cellular vertebrate organisms, a category that includes both human and non-human mammals.

Mimetic: A molecule (such as an organic chemical compound) that mimics the activity of a protein, such as calreticulin and therapeutically effective variants and fragments thereof. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill, pp. 165-174 and *Principles of Pharmacology* (ed. Munson, 1995), chapter 102 for a description of techniques used in computer assisted drug design.

As noted above, the present invention is based on the discovery that calreticulin and certain fragments of this protein, including the Δ120 calreticulin (Seq. I.D. No. 9), the 180 amino acid N-terminal domain ("vasostatin"; Seq. I.D. No. 4), and the 49 (Seq. I.D. No. 6), 60 (Seq. I.D. No. 8), and 61

(Seq. I.D. No. 5) amino acid fragments have one or more of the following biological activities: (1) the ability to inhibit endothelial cell growth; (2) the ability to inhibit angiogenesis; and (3) the ability to suppress tumor growth. The following discussion explains how these activities were discovered and characterized.

II. Calreticulin and Fragments of Calreticulin Inhibit Endothelial Cell Proliferation A. Endothelial Cell Assays Human and bovine endothelial cells were used for growth inhibition assays, and were prepared as follows:

Fetal bovine heart endothelial cells (American Type Culture Collection, ATCC, Manassas, Va.) were grown through passage 12 in DMEM culture medium (BioWhittaker, Walkersville, Md.) containing 10% heat inactivated fetal bovine serum (BioWhittaker), 100 ng/ml bFGF (R&D Systems, Minneapolis, Minn.), and 5 µg/ml gentamicin (Sigma). For proliferation assays, cells were trypsinized (Trypsin/EDTA, Gibco BRL), washed, suspended in culture medium (DMEM containing 10% heat inactivated fetal bovine serum and 5 µg/ml gentamicin), plated (800 cells/well in 0.2 ml culture medium) in triplicate onto 96 well plates, and incubated for 5 days. DNA synthesis was measured by $^3$H thymidine deoxyribose uptake (0.5 mCi/well, 6.7 Ci/mmol; New England Nuclear, Boston, Mass.) during the last 20-23 hours of culture; cells were detached from the wells by freezing and thawing (Angiolillo et al., *J. Exp. Med.* 182:155-162, 1995).

Human umbilical vein endothelial cells were prepared from umbilical cord by 0.1% collagenase II (Worthington Biochemical Co., Freehold, N.J.) digestion, as described (Gordon et al., In Vitro 19:661-671, 1983), and were grown through passage 5 in M199 culture medium (Sigma) supplemented with 20% newborn calf serum (Sigma), 5% human AB serum, 1.6 mM L-glutamine (GibcoBRL), 50 µg/ml porcine heparin (Sigma), 50 µg/ml ascorbate (Fisher, Fairlawn, N.J.), 15 mM HEPES buffer (Calbiochem-Behring, La Jolla, Calif.), and 15 µg/ml Endothelial Cell Growth Supplement (ECGF; a crude extract of bovine neural tissue containing basic and acidic FGF, Sigma). Endothelial cell purity was greater than 95%, as determined by staining with a rabbit antiserum to human Factor VIII-related antigen (Dako, Carpinteria, Calif.). For proliferation assays, cells were trypsinized, washed, suspended in culture medium (RPMI 1640, BioWhittaker) supplemented with 18% heat-inactivated fetal bovine serum (BioWhittaker) and 18 units/ml porcine heparin (Sigma), and plated ($3.5 \times 10^3$ cells/well in 0.2 ml culture medium) in triplicate cultures into 96-well plates. After incubation for 72 hours, DNA synthesis was measured by $^3$H thymidine deoxyribose uptake during the last 20-23 hours of culture.

B. Identification of Calreticulin as an Endothelial Cell Growth Inhibitor

Using inhibition of bFGF (basic Fibroblast Growth Factor)-induced endothelial cell proliferation as an assay to monitor inhibitory activity, inhibitory compounds were purified from serum-free culture supernatants of the EBV-immortalized cell line VDS-O (maintained as described by Tosato, et al., *J. Immunol.* 137:2037-2042, 1986). For production of conditioned medium, exponentially growing VDS-O cells were washed free of serum, and cultured for 48 hours at the concentration of $2.0 \times 10^6$ cells/ml in serum free PFHM-11 medium (GIBCO/BRL, Grand Island, N.Y.) supplemented with 5 µg/ml gentamicin (Sigma Chemical Co., St. Louis, Mo.). At the end of incubation, cells and debris were removed by centrifugation and sterile filtration (0.45 µ filters), and 6.0 µg/ml Aprotinin (Sigma) was added to the conditioned medium.

After clarification, filtration and concentration, the culture supernatant was purified by four sequential chromatographic steps, including metal chelating affinity, anion exchange, hydrophobic interaction, and anion exchange. Silica gel 60 (EM Science, Gibbstown, N.J.), used for absorption of non-polar substances, was added to the conditioned medium at the concentration of 5 gm/l.

After rotation, the silica was removed, and the conditioned medium was filtered (Ultrapump II, Filtron Technology Corp, Northborough, Mass.) through a membrane with an 8,000 dalton MW cutoff (Ultrasette Omega, Filtron). Concentrated (15 fold) supernatant was exchanged into 10 mM $Na_2HPO_4$/$NaH_2PO_4$, 100 mM NaCl, 0.1 mM imidazole (Sigma) at pH 8.3, and applied to a Chelating Sepharose Fast Flow column ($2.5 \times 30$ cm; Amersham Pharmacia Biotech, Piscataway, N.J.) equilibrated in the same buffer. Bound material was eluted with a 10 mM $Na_2HPO_4$/$NaH_2PO_4$, 100 mM NaCl buffer containing 50 mM imidazole. Active fractions were equilibrated into 20 mM $Na_2HPO_4$/$NaH_2PO_4$ buffer (pH 7.8), and applied to an anion exchange Resource Q column (6 ml; Amersham Pharmacia Biotech) equilibrated with the same buffer. Bound fractions were eluted with a linear gradient of 200 mM to 1.0 M NaCl in $Na_2HPO_4$/$NaH_2PO_4$ buffer, pH 6.25. Active fractions were adjusted to 1.2 M $(NH4)_2SO_4$, and applied to Macro-Prep Methyl Hydrophobic Interaction Chromatography (HIC) column ($2.5 \times 30$ cm; Bio-Rad Laboratories, Hercules, Calif.) equilibrated with 20 mM $Na_2HPO_4$/$NaH_2PO_4$ buffer containing 1.2 M $(NH_4)_2SO_4$, at pH 6.5. Bound material was eluted by a linear decreasing gradient of 1.2 to 0 M $(NH_4)_2SO_4$ in 20 mM $Na_2HPO_4$/$NaH_2PO_4$ buffer. Biologically active fractions were pooled and loaded onto a Mini Q PC 3.2/3 anion exchange column (Amersham Pharmacia Biotech) equilibrated with 20 mM $Na_2HPO_4$/$NaH_2PO_4$ buffer at pH 7.8, mounted on a Smart System (Amersham Pharmacia Biotech) equipped with a superloop. Bound material was eluted by a linear gradient of NaCl (20 mM to 1.0 M) in the starting buffer.

In a representative purification, an initial loading with 340 mg total protein from 16 liters of supernatant yielded 4.5 µg of purified protein. The total biologic activity of the starting supernatant was approximately $44 \times 10^3$ units (a unit being defined as the ½ maximal activity measured in a proliferation assay of fetal bovine heart endothelial cells), and the purified material contained approximately $9 \times 10^3$ units, a recovery of approximately 26% of the original biologic activity. The specific activity (units/mg protein) of the purified material was estimated to be $2 \times 10^6$ units.

The biologically active material was analyzed by two-dimensional gel electrophoresis under reduced conditions followed by Coomassie staining (not shown). Two-dimensional polyacrylamide gel electrophoresis was performed as described (Wirth et al., *Electrophoresis* 16:1946-1960, 1995). Samples for electrophoresis were prepared in buffer containing 8M urea, 20 mM Tris, pH 6.8, 30 mM DTT, 4% CHAPS, and 2% Pharmalytes, pH 3-10. Precast immobilized pH gradient gel strips formulated with nonlinear pH gradients, pH 3-10 NL ($180 \times 3$ mm$\times 0.5$ mm) were purchased from Pharmacia LKB and rehydrated overnight at room temperature in 8M urea, 10 mM DTT, 2% w/v CHAPS, and 2% Pharmalytes, pH 3-10. Second dimension SDS-PAGE was performed using 1.5 mm thick 10% SDS polyacrylamide gels at constant current (40 mA/gel) at 10° C. For SDS-PAGE and Western blot analysis, protein was solubilized in Tricine SDS sample buffer (Novex San Diego, Calif.), boiled, and run through 10-20% Tricine Gels. Prestained molecular weight protein standards (range 4-250 kDa, Novex) were used throughout. Gels were stained with Colloidal Coomassie G-250 stain (Colloidal Coomassie kit, Novex) or silver stain (SilverXpress staining kit, Novex). Two well defined polypeptide spots were identified with approximate molecular weight of 55 and 20 kDa and apparent pI of 4.7 and 5.6, respectively. In addition, a series of poorly defined spots were visualized with relative molecular weights ranging between 30 and 40 kDa.

The well defined spots were subjected to trypsin digestion and the tryptic fragments were analyzed by ion trap mass spectrometry. By this method, the 55 kDa polypeptide was identified as human calreticulin and the 20 kDa polypeptide as the light chain of human ferritin.

Further evidence of the identity of the 55 kDa component to calreticulin was obtained by Western blotting of the purified material. After electrophoresis, protein was transferred onto Immobilon-P membranes (Millipore, Bedford, Mass.). For detection of calreticulin, the membranes were incubated overnight with a rabbit anti-human calreticulin antiserum (Affinity Bioreagents Inc., Golden, Colo.), a rabbit anti-calreticulin N, or anti-calreticulin P domain antiserum (Pogue et al., *J. Virol.* 67:7106-7117, 1993). Bound antibody was detected with an affinity-purified, peroxidase-linked, donkey anti-rabbit IgG antibody (Amersham Pharmacia Biotech, Inc., Piscatway, N.J.) and a chemiluminescence detection system (ECL kit, Amersham Pharmacia Biotech).

To gain further insight on the nature of these calreticulin fragments, antisera for human calreticulin N-terminal (aa 6-19) and C-terminal (aa 382-400) peptides were used in immunoblotting (Pogue et al., *J. Virol.* 67:7106-7117, 1993). Both these antisera identified the 55 kDa band and thus confirmed its identity to calreticulin. However, only the antiserum to the N-terminal calreticulin peptide reacted with the 30-40 kDa bands. Therefore, the biologically active, purified material from culture supernatant of the VDS-O cell line contained human calreticulin, the light chain of human ferritin, and N-terminal fragments of calreticulin. This result led to the investigation of other activities of calreticulin and calreticulin fragments, including the 180 amino acid N-terminal domain fragment ("vasostatin"; Seq. I.D. No. 4), Δ120 calreticulin (Seq. I.D. No. 9), the 49 (Seq. I.D. No. 6), 60 (Seq. I.D. No. 8) and 61 (Seq. I.D. No. 5) amino acid fragments, as described below.

III. Production of Recombinant Calreticulin and Calreticulin Fragments

The expression of human calreticulin, the calreticulin N-terminal deletion fragment lacking amino acids 1-120 (Seq. I.D. No. 9), and the N-terminal domain (Seq. I.D. No. 4) fused to maltose-binding protein (MBP) in *Escherichia coli* was previously reported (Singh et al., *Proc. Natl. Acad. Sci. U.S.A.* 91:12770-12774, 1994; Atreya et al., *J. Viroli.* 69:3848-3851, 1995). *E. coli* cells containing the clones described in Singh et al., *Proc. Natl. Acad. Sci. U.S.A.* 91:12770-12774, 1994 and Atreya et al., *J. Viroli.* 69:3848-3851, 1995 were grown in Luria-Bertani broth (Advanced Biotechnologies, Inc., Columbia Md.) with 0.2% glucose and 100 μg/ml ampicillin (Sigma) to an $OD_{600}$ Of approximately 1.0, and fusion protein expression was induced with 0.3 mM IPTG (GIBCO/BRL) for 2-2.5 hours. After lysis (1 μg/ml lysozyme in 10 mM Tris, pH 7.5, 5% glycerol, 100 mM EDTA, 5 mM B-ME), sonication, and centrifugation (30 min at 8360×g) of the bacterial suspension, the supernatant was loaded onto a preequilibrated (20 mM Tris, pH 7.5, 200 mM NaCl, and 1 mM EDTA) 15 ml amylose column (New England Biolabs, Beverly, Mass.), and the bound material was eluted with 10 mM Maltose. Protein-containing fractions were ultracentrifuged (2 hours at 104,000×g); supernatant was retained. Separation of MBP from calreticulin (Seq. I.D. No. 2) and vasostatin (Seq. I.D. No. 4) was accomplished by cleavage with factor Xa (New England Biolabs, Beverly, Mass.). Purification of cleaved calreticulin (Seq. I.D. No. 2) or vasostatin (Seq. I.D. No. 4) from MBP was achieved by anion exchange chromatography using a preequilibrated (20 mM Tris, pH 8.0, 25 mM NaCl) Resource Q column (Amersham Pharmacia Biotech). Bound material was eluted by a step-wise gradient where MBP elutes at 100-150 mM NaCl; Factor Xa elutes at approximately 400 mM NaCl; and calreticulin or vasostatin elute at approximately 250 mM NaCl.

For expression of the calreticulin fragment encompassing amino acids 120-180 (Seq. I.D. No. 5), the coding region for this fragment was amplified by PCR and then cloned (confirmed by sequencing) as an N-terminal fusion protein with the MBP gene for expression in *E. coli*. The growth of *E. coli* and protein purification were performed as described above for MBP-calreticulin.

A recombinant form of calreticulin fused to glutathione S-transferase (GST) was also produced. For construction of the GST-calreticulin fusion construct, the coding region for the mature calreticulin protein was cloned as a C-terminal translational fusion with the glutathione S transferase (GST) gene for expression in *E. coli*. The growth of *E. coli*, the induction and release of GST-calreticulin (Seq. I.D. No. 2) from the bacteria was the same as described above for MBP-calreticulin, except for IPTG induction (0.6 mM). For purification of GST-calreticulin, the bacteria were sonicated, pelleted, and the supernatants (adjusted to pH 7.0) were mixed with prewashed Glutathione Sepharose 4B (Bulk GST purification module; Amersham Pharmacia Biotech) in PBS with 1.0% Triton X-100. After 30 min incubation and washing the beads, bound protein was eluted with a 50 mM Tris-HCl buffer containing 10 mM glutathione, pH 8.0. Eluted material was ultracentrifuged (2 hours at 104,000×g), and supernatant retained. All protein lots for in vivo and in vitro experiments (GST-calreticulin, control GST, MBP-calreticulin, MBP-vasostatin, MBP, cleaved calreticulin and vasostatin) were tested for endotoxin by the Limulus Amebocyte Lysate (LAL) kinetic-QCL™ assay (BioWhittaker) and were found to contain <5 units/10 μg protein.

The purified recombinant proteins including the expression tag sequences were resolved by SGS-PAGE as discrete bands migrating at the expected relative positions. Calreticulin, cleaved from MBP-calreticulin by treatment with Factor Xa and subsequently purified by anion exchange chromatography, resolved as a doublet with a relative molecular weight of approximately 50 and 55 kDA.

Natural calreticulin was also obtained from purified B cell line supernatant by eluting the band at 55 kDa from a preparative Tris-glycine gel. SDS PAGE analysis and silver staining documented the isolation of a doublet at approximately 55 kDA from other copurified components.

When tested in functional assays, recombinant purified MBP-calreticulin (Seq. I.D. No. 2) inhibited the proliferation of fetal bovine heart endothelial cells induced by bFGF. At a concentration of 1 μg/ml, MBP-calreticulin (Seq. I.D. No. 2) inhibited fetal bovine heart endothelial cell growth by 67% while control MBP had minimal effects (FIG. 1). Similar inhibition was noted with 1 μg/ml GST-calreticulin (Table 1). In addition, recombinant calreticulin (Seq. I.D. No. 2) that had been cleaved and purified from MBP-calreticulin, as well as purified natural calreticulin inhibited the proliferation of fetal bovine heart endothelial cells, while control MBP did not (Table 1). By contrast, recombinant purified light chain of human ferritin (a gift from Dr. P. Arosio, San Raffaele, Milan, Italy) had minimal effect on the proliferation of endothelial cells when tested at 1 pg to 1 μg/ml (not shown).

To assess whether specific fragments of calreticulin exhibit inhibitory activity, the components from cell line culture supernatants with a relative molecular weight of 30-40 kDa which were immunoreactive with antisera to calreticulin were isolated by gel elution. A component with a relative molecular weight of approximately 34 kDa was separated from calreticulin at 55-60 kDa. This gel-eluted calreticulin fragment inhibited endothelial cell proliferation (Table 1). Thereafter, the N-terminal calreticulin domain (Seq. I.D. No. 4), including amino acids 1-180 of the mature protein, was produced in *E. coli* as a fusion protein of MBP (MBP-calreticulin-N, Atreya et al., *J. Viroli.* 69:3848-3851, 1995). The purified recombinant MBP-calreticulin N-terminal domain and the cleaved calreticulin N-terminal domain inhibited the proliferation of fetal bovine heart and of human umbilical vein endothelial cells (Table 2).

TABLE 1

Inhibition of Endothelial Cell Proliferation by Calreticulin

| | Additions to Culture | Proliferation mean cpm/culture (±SD) | Inhibition (%) |
|---|---|---|---|
| 1. | None | 5,731 (2344)[a] | |
| | bFGF | 23,243 (8630) | |
| | GST-Calreticulin | 12,503 (4510) | 46 |
| | GST | 25,410 (8158) | |
| 2. | None | 5,510 (2040)[b] | |
| | bFGF | 25,322 (7849) | |
| | Cleaved calreticulin | 7,088 (1846) | 72 |
| | Cleaved MBP | 21,410 (232) | |
| 3. | None | 15,277[c] | |
| | bFGF | 57,613 | |
| | Gel-eluted calreticulin | 11,226 | 81 |
| | Gel-eluted calreticulin fragment | 32,039 | 45 |
| | Gel-eluted control | 67,796 | |

Fetal bovine heart endothelial cells (800 cells/well) were cultured for 5 days in medium alone or medium supplemented with bFGF (25 ng/ml). Recombinant purified GST-calreticulin (Seq. I.D. No. 2; 1 μg/ml), control recombinant GST (1 μg/ml), calreticulin cleaved and purified from MBP-calreticulin (Seq. I.D. No. 3; 1 μg/ml), MBP cleaved and purified from MBP-calreticulin (1 μg/ml), natural calreticulin(estimated concentration 0.160 μg/ml) or natural fragments of calreticulin (estimated concentration 0.8 μg/ml) derived by gel elution of calreticulin (purified from cell line culture supernatant) were added to endothelial cell cultures with bFGF (25 ng/ml). Proliferation was measured by $^3$H thymidine incorporation during the final 20-23 hours of culture; the results reflect mean cpm/culture.
[a]Reflects the mean of 9 experiments, each performed in triplicate
[b]Reflects the mean of 2 experiments, each performed in triplicate
[c]Reflects the mean of triplicate cultures; SDs within 12% of the mean

TABLE 2

Inhibition of Endothelial Cell Proliferation by Vasostatin

| | Additions to Culture | Proliferation (mean cpm/culture) | Inhibition (%) |
|---|---|---|---|
| 1.[a] | None | 142 | |
| | bFGF | 32,493 | |
| | MBP-vasostatin | 17,930 | 44.8 |
| | MBP | 34,363 | |
| | Vasostatin | 13,231 | 59.3 |
| 2.[b] | None | 4,210 | |
| | bFGF | 28,050 | |
| | Vasostatin | 9,864 | 64.8 |

Human umbilical vein endothelial cells (3.5 × 10³ cells/well) or fetal bovine heart endothelial cells (800 cells/well) were cultured in medium alone or in medium supplemented with bFGF. Recombinant purified vasostatin (1 μg/ml), MBP-vasostatin (1 μg/ml), or MBP (1 μg/ml) were added to bFGF-supplemented cultures. Proliferation was measured by $^3$H thymidine incorporation during the final 20-23 hours of culture.
[a]Cultures containing human umbilical cord derived endothelial cells; bFGF used at 25 ng/ml. The results reflect the mean of triplicate cultures; SDs within 10% of the mean.
[b]Cultures containing fetal bovine heart endothelial cells; bFGF 25 ng/ml. The results reflect the mean of 3 experiments; SDs within 12% of the mean.

Smaller fragments of the calreticulin N-terminal domain were then synthesized. These fragments were tested for activity against fetal bovine heart endothelial cells as described above. Both were found to be active, with the 49 amino acid fragment (Seq. I.D. No. 6) producing 45-69% inhibition at a concentration of 50 μg/ml and the 60 amino acid fragment (Seq. I.D. No. 8) producing 59.5-88% inhibition at a concentration of 100 μg/ml (Table 3). It should be noted that a control peptide 60 amino acids in length (from the chemokine RANTES) which was similarly synthesized and purified, had no inhibitory effect in these assays. It should also be noted that the levels of endothelial cell growth inhibition by the 49 (Seq. I.D. No. 6) and the 60 (Seq. I.D. No. 8) amino acid fragments were comparable to those derived from vasostatin (Seq. I.D. No. 4). The higher amounts of peptide being required to achieve endothelial cell growth inhibition compared to vasostatin (Seq. I.D. No. 4) are likely attributable to the differences in the manufacturing process resulting in peptide denaturing and/or unfavorable folding. To ensure that growth inhibition of endothelial cell growth in vitro was not the result of non-specific toxicity, the 49 (Seq. I.D. No. 6) and the 60 (Seq. I.D. No. 8) amino acid fragments were tested for their effects on the proliferation of 2 indicator B cells lines, VDS-O and CA-46. At concentrations ranging between 1-100 μg/ml, the 49 (Seq. I.D. No. 6) and the 60 (Seq. I.D. No. 8) amino acid fragments had minimal effect on the proliferation of these cell lines.

Figure 4:
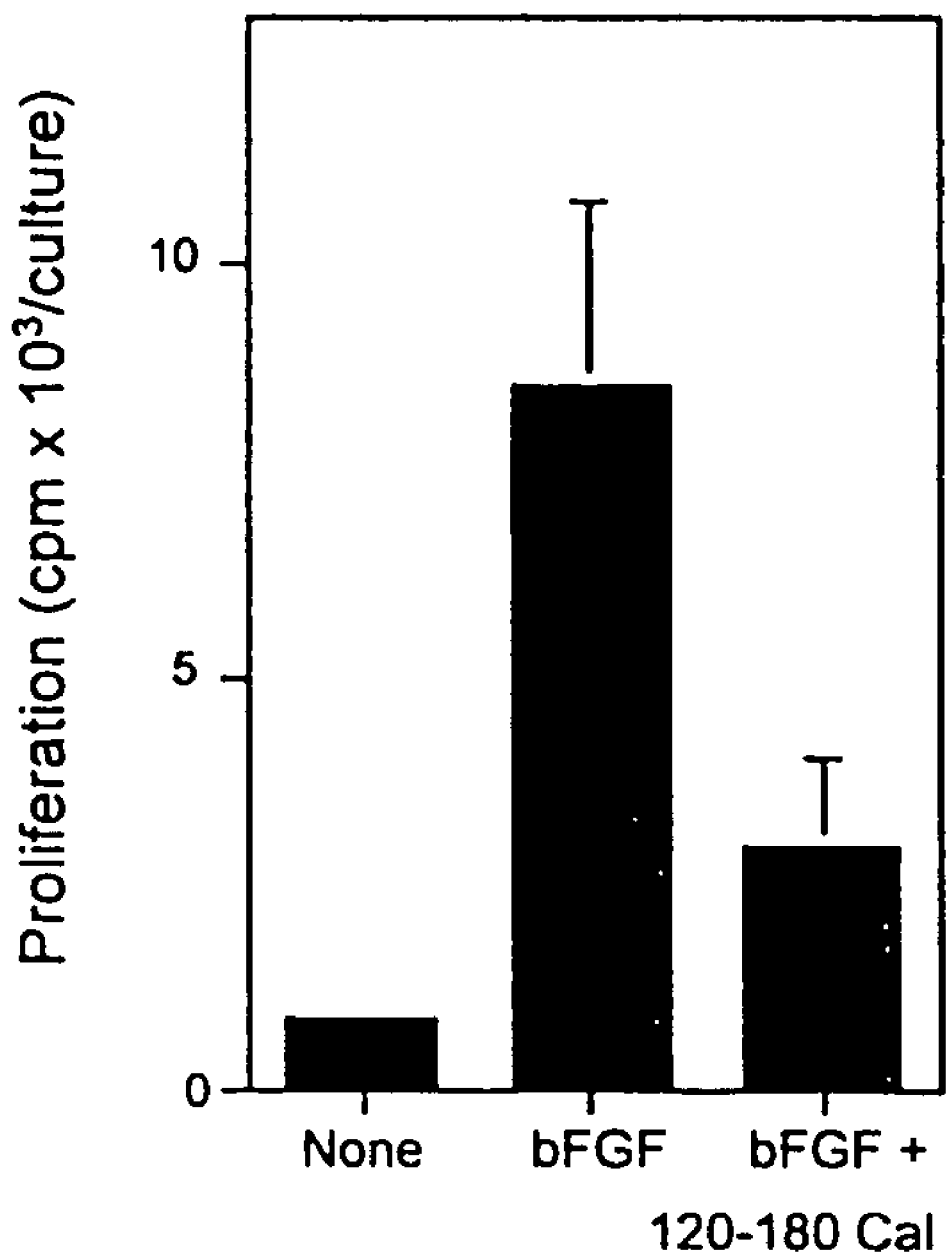
FIG. 4 is a graph showing the inhibition of endothelial cell proliferation by the 61 amino acid calreticulin fragment MBP-120-180 calreticulin (Seq. I.D. No. 5). Fetal bovine heart endothelial cells (800 cells/well) were incubated for 5 days either in medium alone or medium supplemented with bFGF (15 ng/ml), with or without the recombinant purified 61 amino acid fragment (Seq. I.D. No. 5) (both at 1 μg/ml). The results of 8 experiments are expressed as mean cpm (±SD).

To further ensure that fragments of calreticulin are active as inhibitors of endothelial cell growth, recombinant MBP-Δ120 calreticulin (calreticulin missing the N-terminal 1-120 amino acids; Seq. I.D. No. 9) and MBP-120-180 calreticulin (Seq. I.D. No. 5) were tested. Recombinant purified MBP-Δ120 calreticulin (Seq. I.D. No. 9) inhibited the proliferation of fetal bovine heart endothelial cells, and the degree of inhibition was comparable to that of calreticulin (FIG. 4).

Figure 5:
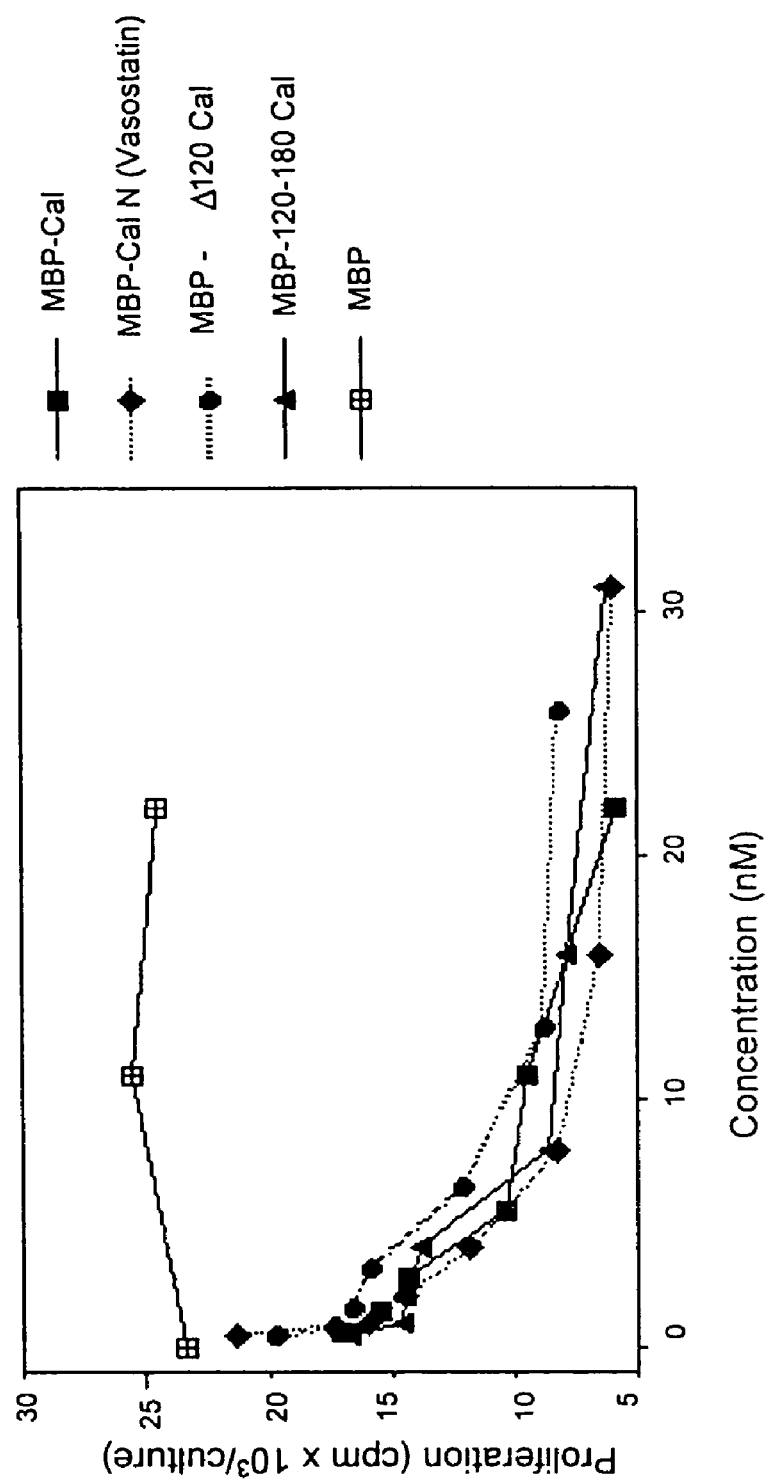
FIG. 5 shows a graph comparing endothelial cell growth inhibition by MBP calreticulin (Seq. I.D. No. 3), MBP-Δ120 calreticulin (Seq. I.D. No. 9), MBP-vasostatin (Seq. I.D. No. 4), and MBP-120-180 calreticulin fragment (Seq. I.D. No. 5). Fetal bovine heart endothelial cells (800 cells/well) were cultured for 5 days in medium alone or medium supplemented with bFGF (15 ng/ml). Recombinant purified fusion proteins were added to culture at 0.4-32 nM concentrations to bFGF-supplemented cultures. Proliferation was measured by $^3$H thymidine incorporation during the final 20-23 hours of culture. The results reflect the mean of triplicate cultures; SDs within 15% of the mean. The mean response of endothelial cells was 2,217 c.p.m. when cultured in medium alone, and 23,377 c.p.m. when cultured with bFGF alone.
Figure 6A:
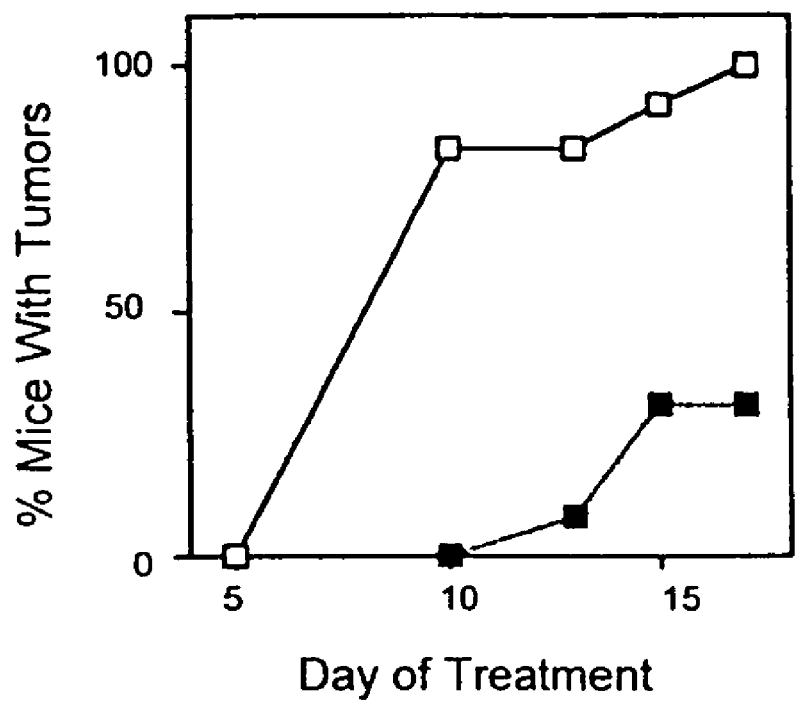
FIGS. 6A, 6B, 6C and 6D are graphs showing the inhibition of tumor growth by vasostatin (Seq. I.D. No. 4) and calreticulin (Seq. I.D. No. 3). Burkitt lymphoma cells (CA46 cell line, 1×10$^7$ cells) were inoculated subcutaneously (s.c.) into BALB/c athymic mice, 6 weeks of age. Beginning on the day of cell inoculation and continuing thereafter daily, 6 days/week, mice were inoculated s.c. with either control buffer (open symbols) or test protein (closed symbols). The results reflect the % mice with tumor as a function of time. A. 12 mice were inoculated with control purified GST protein (Seq. I.D. No. 2; 20 μg/day×14 days), and 13 mice were inoculated with purified GST-calreticulin (Seq. I.D. No. 3; 60 μg/day×14 days). B. 8 mice were inoculated with control purified MBP protein (20 μg/day×14 days), and 9 mice were inoculated with purified MBP-vasostatin (30 μg/day×14 days). C. 12 mice were inoculated with control purified MBP (40 μg/day×18 days), and 12 mice were inoculated with MBP-vasostatin (60 μg/day×18 days); all mice with tumor (12 treated with MBP and 4 treated with MBP-vasostatin) were killed on day 18. The remaining mice were observed up to day 60. D. 6 mice were treated with formulation buffer alone (0.1 ml/day×22 days, open circles), 5 mice were treated with 20 μg/day×22 days purified MBP-vasostatin (Seq. I.D. No. 4; diamonds), and 9 mice were treated with 100 μg/day×22 days purified MBP-vasostatin (Seq. I.D. No. 4; squares).
Figure 6B:
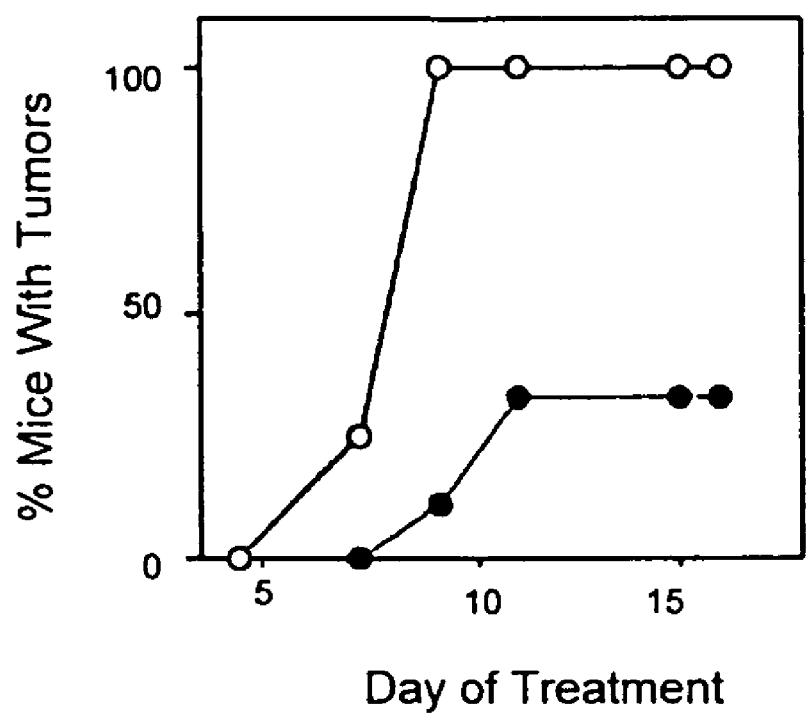
Figure 6C:
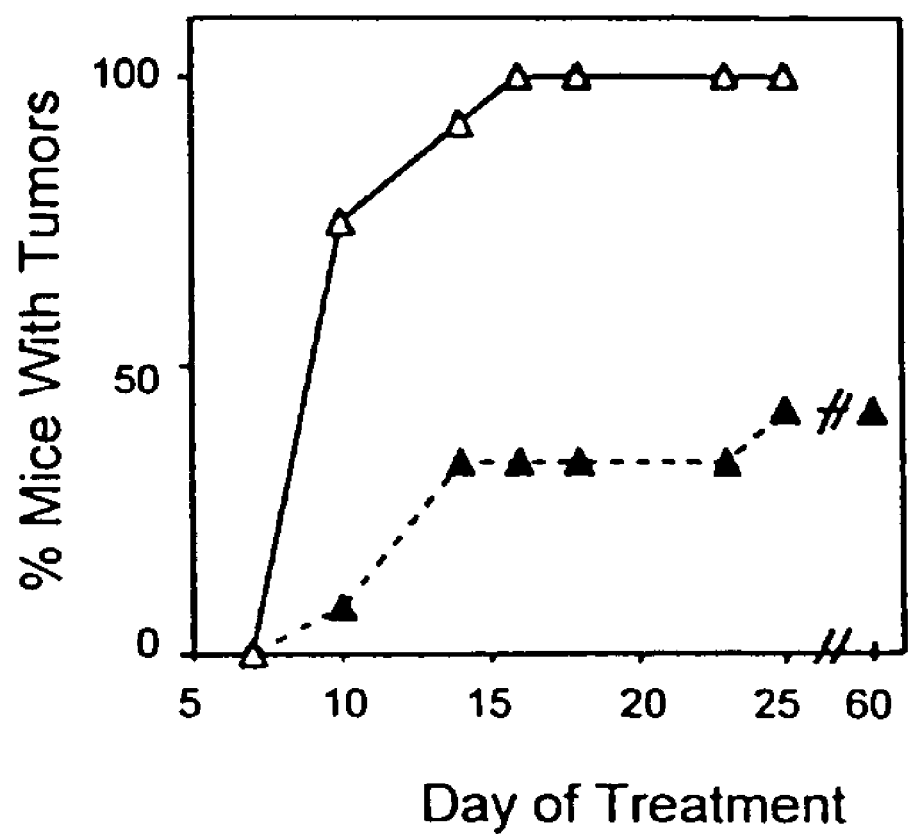
Figure 6D:
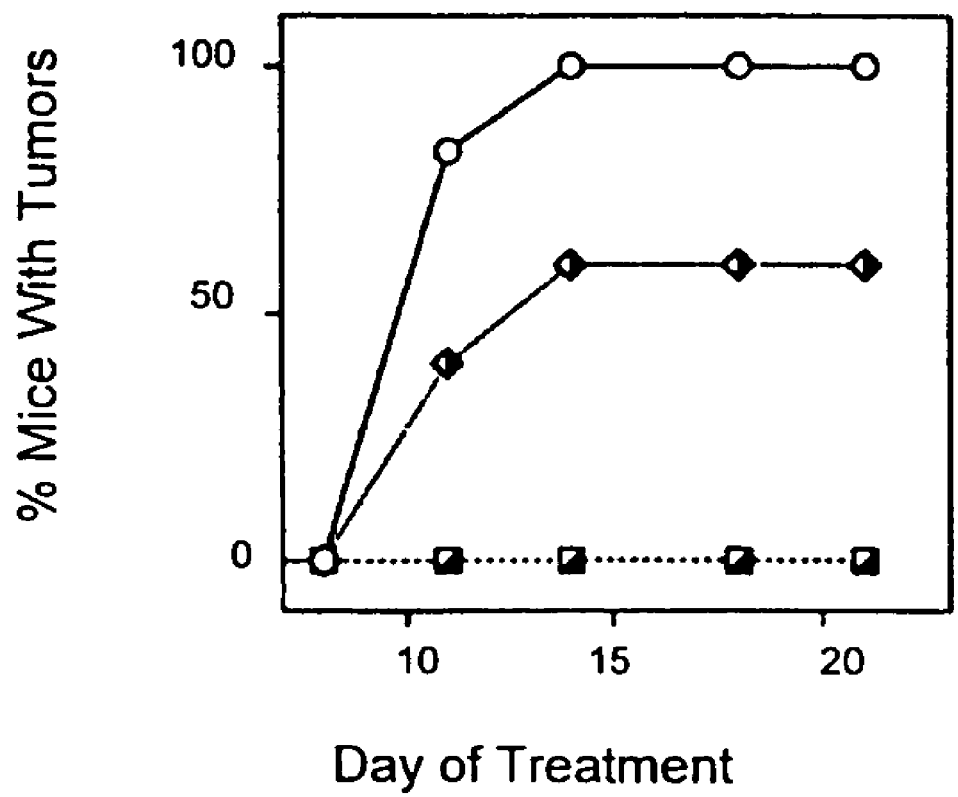
Figure 7A:
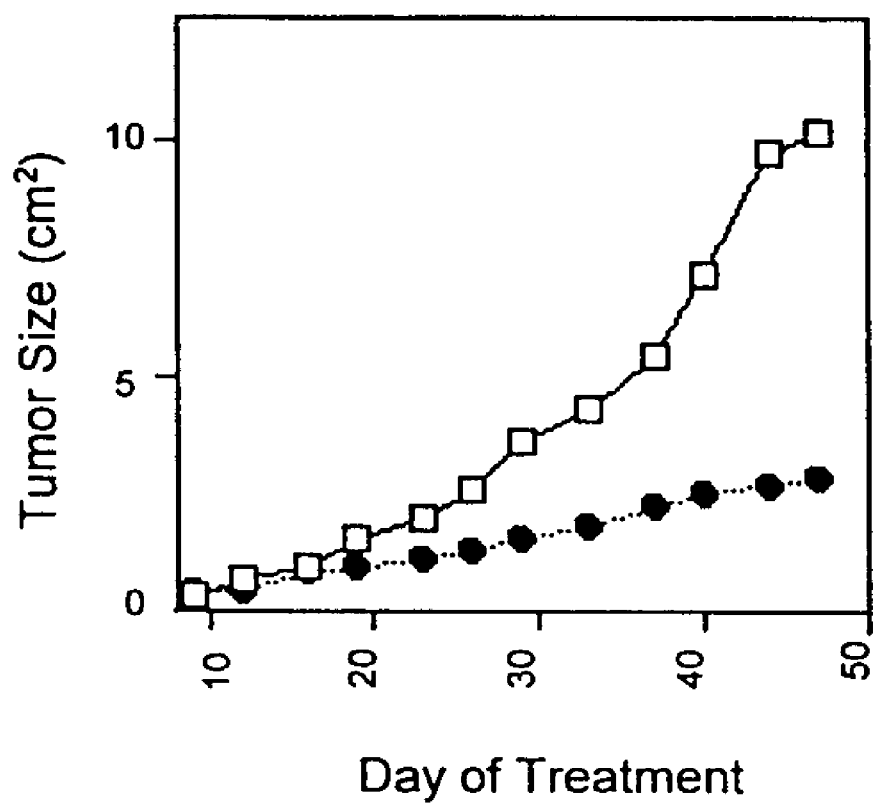
FIGS. 7A and 7B are graphs showing the inhibition of established Burkitt tumor growth by vasostatin. Burkitt lymphoma cells (CA46 cell line, 1×10$^7$ cells) were inoculated s.c. into BALB/c athymic mice, 6 weeks of age. A. After a tumor appeared (at least 160 mm$^2$ in size), 9 mice were treated with MBP-vasostatin (Seq. I.D. No. 4; 200 μg/day, 6 days/week, 100 μl/dose×46 days) and 10 mice were treated with formulation buffer alone (100 μl×46 days). Tumor size was recorded. Formulation buffer (open squares); MBP-vasostatin (Seq. I.D. No. 4; closed circles) B. After a tumor appeared (at least 160 mm$^2$ in size), 12 mice were treated with MBP-vasostatin (Seq. I.D. No. 4; 200 μg/twice/day, 5 days/week and once/day 2 days/week, 100 μl/dose×26 days) and 8 mice were treated with formulation buffer alone (100 μl×26 days). The % mice with tumor was determined. Formulation buffer (open squares); MBP vasostatin (Seq. I.D. No. 4; closed squares).
Figure 7B:
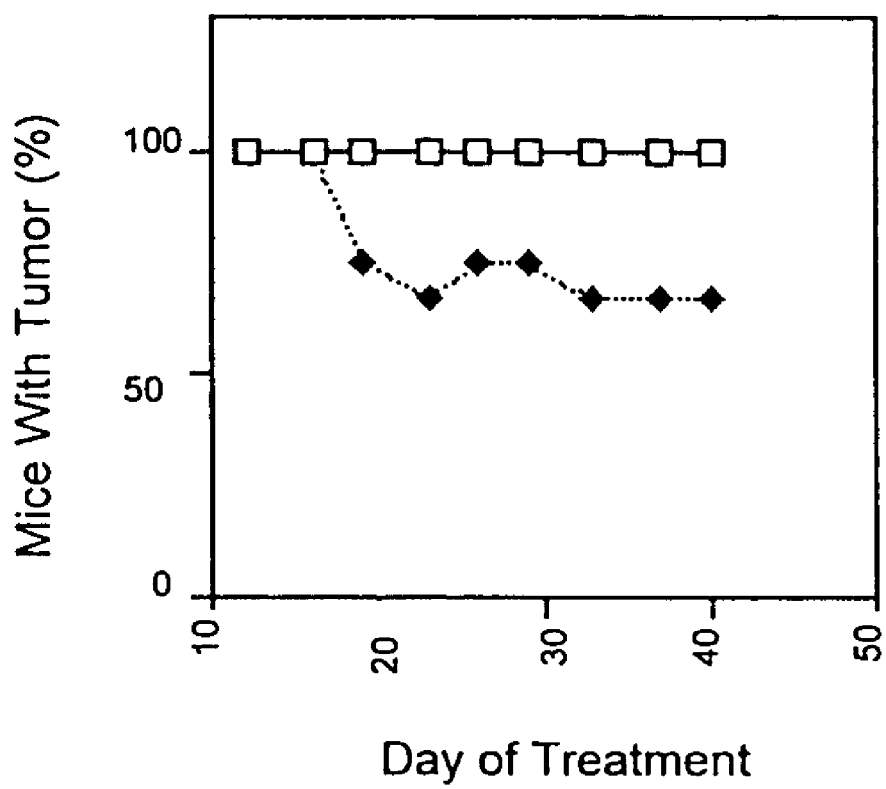

Vasostatin (calreticulin N-domain, encompassing amino acids 1-180; Seq. I.D. No. 4), full length calreticulin (Seq. I.D. No. 2), calreticulin minus 17 amino acids from the N-terminus (Seq. I.D. No. 3), and Δ120 calreticulin (Seq. I.D. No. 9) inhibited bFGF-induced endothelial cell proliferation to a similar degree at similar concentrations. Hence, the activity of the 61 amino acid calreticulin fragment (Seq. I.D. No. 5) was also determined. This was done by purifying the MBP-120-180 calreticulin fragment (Seq. I.D. No. 5) from *E. coli* expressing the recombinant protein fused to MBP (FIG. 5A). When tested for inhibition of endothelial cell proliferation, recombinant purified MBP-120-180 calreticulin fragment (Seq. I.D. No. 5) inhibited the proliferation of bovine heart endothelial cells induced by bFGF (FIG. 5B). At a concentration of 0.5 µg/ml, the 61 amino acid calreticulin fragment (Seq. I.D. No. 5) inhibited fetal bovine heart endothelial cell proliferation by 65%. A side-by-side comparison of full length MBP-calreticulin (Seq. I.D. No. 2), MBP-vasostatin (Seq. I.D. No. 4), MBP-Δ120 calreticulin (Seq. I.D. No. 9) and MBP-120-180 calreticulin (Seq. I.D. No. 5) fragment revealed that, on a molar basis, the four proteins display similar endothelial cell growth inhibitory active in vitro. Control MBP was not inhibitory (FIG. 6).

Hence, both the calreticulin fragment identified as Seq. I.D. No 5 (the 61 amino acid peptide) and the calreticulin fragment identified as Seq. I.D. No 6 (the 49 amino acid peptide) specifically inhibit endothelial cell growth in vitro.

TABLE 3

Inhibition of Endothelial Cell Proliferation by Calreticulin 60 and 49 amino acid fragments

| | Addition to Culture | Proliferation (mean cpm/culture) | Inhibition (%) |
|---|---|---|---|
| 1. | None | 5,290[a] | |
| | bFGF | 13,950 | |
| | MBP-vasostatin | 8,585 | 38.5 |
| | 60 amino acid peptide (100 µg/ml)[b] | 1,688 | 87.9 |
| | 60 amino acid peptide (50 µg/ml) | 8,318 | 40.1 |
| | 49 amino acid peptide (50 µg/ml)[c] | 4,368 | 68.7 |
| | 49 amino acid peptide (25 µg/ml) | 6,037 | 56.7 |
| | 49 amino acid peptide (12.5 µg/ml) | 9,743 | 30.2 |
| | RANTES (100 µg/ml) | 16,443 | |
| 2. | None | 4,434 | |
| | bFGF | 9,160 | |
| | 60 amino acid peptide (100 µg/ml) | 3,709 | 59.5 |
| | 49 amino acid peptide (50 µg/ml) | 5,004 | 45.4 |
| | RANTES (50 µg/ml) | 10,291 | |
| | RANTES (12.5 µg/ml) | 13,644 | |

Fetal bovine heart endothelial cells (800 cells/well) were cultured for 5 days in medium alone or medium supplemented with bFGF (25 ng/ml). Recombinant MBP vasostatin (0.5 µg/ml), a synthetic calreticulin 60 amino acid peptide (50 and 100 µg/ml), a synthetic calreticulin 49 amino acid peptide (12.5-50 µg/ml), and a synthetic 60 amino acid peptide of the chemokine RANTES (12.5-100 µg/ml) were added to endothelial cell cultures with bFGF (25 µg/ml). Proliferation was measured by $^3$H thymidine incorporation during the final 20-23 hours of culture; the results reflect the mean cpm/culture.
[a]Reflects the mean of triplicate cultures; SDs within 10% of the mean.
[b]The 60 amino acid calreticulin peptide (amino acids 121-180) is identified as Seq. I.D. No 8
[c]The 49 amino acid calreticulin peptide (amino acids 132-180) is identified as Seq. I.D. No. 6

IV. Calreticulin and Calreticulin Fragments do not Inhibit Growth of Nonendothelial Cells Following the observation that calreticulin and calreticulin fragments inhibit the proliferation of endothelial cells, these proteins were then assayed for inhibitory effect on non-endothelial cell types.

Human mononuclear cells, and mononuclear cells enriched for T or B lymphocytes, were used in proliferation assays in the presence of phytohemagglutinin (Sigma), pokeweed-mitogen (Sigma), or Epstein-Barr virus (B95-8 strain), as described (Tosato et al., *J. Immunol.* 140:4329-4336, 1988). The lymphoblastoid cell line VDS-O (Tosato, et al., *J. Immunol.* 137:2037-2042, 1986); the Burkitt lymphoma cell lines CA46, BL41, KK124, Ag876, SHO (Cherney et al., *Cancer Res.* 57:2508-2515, 1997); the T-cell line Molt-4 (ATCC); the Hodgkin's lymphoma cell line Hs445 (ATCC); the prostate adenocarcinoma cell lines TSU-Pr1 (from A. Passaniti, NIH, Baltimore, Md.), Du145 (ATCC), and PC3 (ATCC); and the acute promyelocytic leukemia cell line HL-60 (ATCC) were cultured in RPMI 1640 medium with 10% heat inactivated fetal calf serum (BioWhittaker), 20 mM L-glutamine (Sigma) and 5 µg/ml gentamicin, and tested in 3-5 day proliferation assays at cell densities ranging from 300 to 2400 cells/well. All other cell lines were tested for proliferation in 3-day assays. The neuroblastoma cell line SKNMC (ATCC) was cultured in EMEM medium (BioWhittaker) with 10% heat inactivated fetal calf serum (BioWhittaker) and 5 µg/ml gentamicin (Sigma) and tested for proliferation at 125-1000 cells/well. The lung adenocarcinoma cell line A549 (ATCC) was cultured in F-12 Nutrient Mixture (HAM, GIBCO BRL) with 10% heat inactivated fetal calf serum (BioWhittaker) and 5 µg/ml gentamicin (Sigma), and tested for proliferation at 250-2000 cells/well. The breast adenocarcinoma MDA-MB-468 (ATCC) and the Wilms tumor SK-NEP-1(ATCC) cell lines were cultured in Leibovitz L-15 medium (GIBCO BRL) supplemented with 10% heat inactivated fetal calf serum (BioWhittaker) and 5 µg/ml gentamicin (Sigma), and tested for proliferation at 300-2500 cells/well. The colon carcinoma cell line SW480 (ATCC), the melanoma cell line A-375 (ATCC), and human foreskin fibroblasts (H568, ATCC) were cultured in DMEM medium (BioWhittaker) with 10% heat inactivated fetal calf serum (BioWhittaker) and 5 µg/ml gentamicin (Sigma), and were tested for proliferation at 500-4000 cells/well. All cell lines tested mycoplasma negative.

The results of these assays showed that, in contrast to their inhibitory effect on human and bovine endothelial cell growth, calreticulin (Seq. I.D. No. 2) and the calreticulin N-terminal 180 amino acid fragment (Seq. I.D. No. 4) had minimal effect on the proliferation of a variety of other primary cells and cell lines, when administered at concentrations of 0.5-2.5 µg/ml.

The 61 amino acid fragment of calreticulin (calreticulin 120-180; Seq. I.D. No. 5), as well as the 60 and 49 amino acid peptides of calreticulin (Seq. I.D. No. 8, and 6, respectively) were also tested for their ability to inhibit the proliferation in vitro of cells other than endothelial cells. At concentrations ranging between 1 and 100 µg/ml, neither peptide inhibited the proliferation of the human B cell lines VDS-O and CA-46. Thus, calreticulin (Seq. I.D. No. 2), the calreticulin N-terminal 180 amino acid fragment, vasostatin (Seq. I.D. No. 4), a 60 amino acid calreticulin peptide included in the N-terminal amino acid peptide (amino acids 121-180; Seq. I.D. No. 8), and a 49 amino acid calreticulin peptide (amino acids 132-180; Seq. I.D. No. 6) included in the N-terminal 180 amino acid peptide specifically inhibit endothelial cell proliferation.

V. Calreticulin and Calreticulin Fragments Inhibit Angiogenesis

The murine Matrigel assay (Passaniti et al., *Lab. Invest.* 67:519-528, 1992) was employed to evaluate the effects of calreticulin and calreticulin fragments on angiogenesis in vivo. The Matrigel assay was performed as described by Angiolillo et al. (*J. Exp. Med.* 182:155-162, 1995). Matrigel, a crude extract of the Englebreth-Holm-Swarm tumor, was obtained from Collaborative Biomedical Products, Becton Dickinson Labware, Bedford, Mass. An aliquot (0.5 ml) of Matrigel alone or with desired additives was injected subcutaneously (s.c.) into the mid abdominal region of female BALB/c nude mice, 6-8 weeks old. Five mice were injected with each mixture. After 5-7 days, the animals were sacrificed, Matrigel plugs were removed, fixed in 10% neutral buffered formalin solution (Sigma), and embedded in paraffin. Tissues were sectioned (5 µthickness), and slides stained with Masson's trichrome. Quantitative analysis of angiogenesis in Matrigel plugs utilized a computerized semi-automated digital analyzer (Optomax, 40-10 System, Hollis, N.H.). The instrument was adjusted to evaluate a circular area measuring $1.26 \times 10^5$ mm$^2$ of Matrigel, and within this area, to measure the area occupied by cells. For each plug, 12-15 distinct fields were evaluated. The fields were randomly selected from each plug, and the operator was blind to the experimental design. The average area occupied by cells/$1.26 \times 10^5$ mm$^2$ Matrigel field was calculated. Results are expressed as the mean area occupied by cells/Matrigel field.

Matrigel plugs were fixed in 10% neutral buffered formalin solution (Sigma), embedded in paraffin, sectioned at 4 µm, and stained with Masson's trichrome by standard methods.

When added to Matrigel at concentrations of 1.25-5 µg/ml, GST-calreticulin (Seq. I.D. No. 2) displayed a concentration-dependent inhibition of bFGF-induced neovascularization (Table 4, exp. 1). Similarly, at 5-10 µg/ml, the MBP-1-180 amino acid fragment (termed "vasostatin" because of this activity; Seq. I.D. No. 4) inhibited bFGF-induced neovascularization (Table 4, exp. 2). In addition, at 5 µg/ml, vasostatin (cleaved and purified from MBP-vasostatin) inhibited bFGF-induced Matrigel vascularization comparably to MBP-vasostatin and MBP-calreticulin (Table 4, exp. 3).

Furthermore, MBP-Δ120 calreticulin (Seq. I.D. No. 9) and 120-180 calreticulin (Seq. I.D. No. 5) inhibited bFGF-induced Matrigel vascularization comparably to cleaved recombinant calreticulin (Table 4, exp. 4).

VI. Calreticulin and Calreticulin Fragments Inhibit Tumor Growth

Calreticulin and calreticulin fragments were initially tested for their ability to prevent the growth of human Burkitt lymphomas in athymic mice.

BALB/c nu/nu female mice, 6 weeks of age (National Cancer Institute, Frederick, Md.) maintained in pathogen-limited conditions, received 400 rad (1 rad=0.01 Gy) total body irradiation and 24 hours later were injected s.c. in the right abdominal quadrant with $10^7$ exponentially growing human Burkitt lymphoma cells (CA46 cell line; Sgadari et al., *Proc. Natl. Acad. Sci. U.S.A.* 93:13791-13796, 1996) in 0.2 ml PBS. Immediately after the Burkitt cells were inoculated s.c., and continuing daily thereafter 6 days/week, the mice received s.c. injections proximal to the site of original cell inoculation of test calreticulin samples or appropriate controls. These included purified GST-calreticulin (Seq. I.D. No. 3), control GST, MBP-calreticulin (Seq. I.D. No. 2), MBP-vasostatin (Seq. I.D. No. 4), MBP, or formulation buffer used to dilute test proteins (sterile saline solution containing 50 mg/ml human albumin and 5 mg/ml mannitol; endotoxin <5 units/ml). Tumor size was estimated (in cm$^2$) twice weekly as the product of two-dimensional caliper measurements (longest perpendicular length and width). A subcutaneous mass appearing at or proximal to the site of cell inoculation was considered a tumor when it measured at least 0.16 cm$^2$ in surface area and increased in size by at least 0.1 cm$^2$ over the following week.

As expected, 12/12 mice injected with control GST protein developed a tumor by day 17. By contrast, only 4/13 mice

TABLE 4

| Exp. # | Additions to Matrigel | Mean Surface Area Occupied by Cells (mm$^2$/1.26 × 10$^5$ mm$^2$) | Inhibition (%) |
|---|---|---|---|
| 1. | None | 671 | |
| | bFGF | 17,732 | |
| | bFGF + GST-calreticulin (5 µg/ml) | 4,616 | 74 |
| | bFGF + GST-calreticulin (2.5 µg/ml) | 6,387 | 64 |
| | bFGF + GST-calreticulin (1.25 µg/ml) | 9,870 | 44 |
| 2. | None | 649 | |
| | bFGF | 11,544 | |
| | bFGF + MBP-vasostatin (10 µg/ml) | 4,539 | 61 |
| | bFGF + MBP-vasostatin (5 µg/ml) | 5,286 | 54 |
| | bFGF + MBP (10 µg/ml) | 9,186 | 20 |
| 3. | None | 487 | |
| | bFGF | 14,472 | |
| | bFGF + MBP-calreticulin (5 µg/ml) | 5,112 | 65 |
| | bFGF + MBP-vasostatin (5 µg/ml) | 4,989 | 66 |
| | bFGF + vasostatin (5 µg/ml) | 4,638 | 68 |
| | MBP (5 µg/ml) | 13,472 | 7 |
| 4. | None | 1,329 | |
| | bFGF | 8,320 | |
| | bFGF + cleaved calreticulin | 3,464 | 58 |
| | bFGF + MBP-Δ120 calreticulin | 4,291 | 48 |
| | bFGF + MBP-120-180 | 2,458 | 70 |

Figure 3:
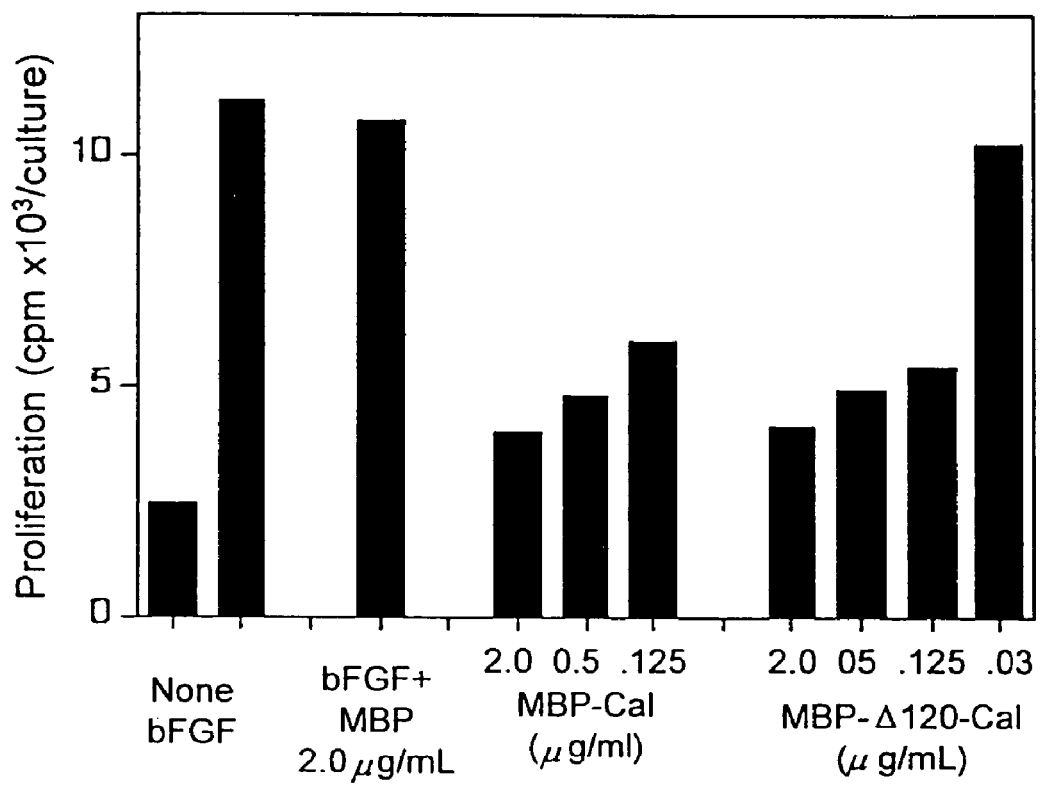
FIG. 3 shows the inhibition of endothelial cell proliferation by Δ120 calreticulin (Seq. I.D. No. 9). Fetal bovine heart endothelial cells (800 cells/well) were cultured for 5 days in medium alone or medium supplemented with bFGF (25 ng/ml). Recombinant purified MBP-calreticulin (Seq. I.D. No. 3), MBP-Δ120 calreticulin (Seq. I.D. No. 9), or MBP were added to bFGF-supplemented cultures. Proliferation was measured by $^3$H-thymidine incorporation during the final 20-23 hours of culture. The results reflect the mean of triplicate cultures; SDs within 12% of the mean.

Mice were injected subcutaneously with Matrigel alone, Matrigel plus bFGF (150 ng/ml), Matrigel plus bFGF (150 ng/ml) plus GST-calreticulin (Seq. I.D. No. 2), MBP-calreticulin (Seq. I.D. No. 3), MBP-vasostatin (Seq. I.D. No. 4), MBP, vasostatin, MBP-Δ120 calreticulin (Seq. I.D. No. 9), or MBP-120-180 calreticulin (Seq. I.D. No. 5). Plugs were removed after 5-7 days, and histologic sections were stained with Masson's trichrome. The results reflect the mean surface area (expressed in mm$^2$) occupied by cells within a circular surface area of 1.26 × 10$^5$ mm$^2$; 12-15 non-overlapping fields were scanned in each plug; there were 5 plugs/group. Determinations of surface area were performed by a semi-automated digitalized analyzer.

injected with GST-calreticulin (Seq. I.D. No. 2) developed a tumor by day 17 (p=0.005) (FIG. 3A). The tumor-bearing mice were sacrificed, and the remaining 9 non-tumor bearing mice were maintained untreated. Tumors eventually developed in 8 of the 9 mice that had received initial calreticulin treatment. The latest tumor developed on day 36, 22 days after treatment had ended. One mouse remains tumor free (>100 days).

Vasostatin (Seq. I.D. No. 4) was tested for its ability to prevent or delay Burkitt tumor growth in the same murine tumor model. In a representative experiment (3 performed), MBP-vasostatin (Seq. I.D. No. 4) was inoculated daily, 6 days/week, for 14 days at a dose of 30 μg/mouse (FIG. 3B). At the end of treatment, 3/9 mice inoculated with MBP-vasostatin (Seq. I.D. No. 4) had developed a tumor, as opposed to 8/8 mice inoculated with control MBP (p=0.009). After treatment was suspended on day 14, all mice were maintained untreated. All but one mouse (tumor free for >100 days) developed a tumor; the latest tumor appeared 15 days after treatment had ended.

The effects of extended vasostatin (Seq. I.D. No. 4) treatment on tumor development were examined (FIG. 3C). All animals received treatment with MBP-vasostatin (60 μg/mouse, daily, 6 days/week; (Seq. I.D. No. 4) for at least 18 days, at which time all animals with tumors were sacrificed. The remaining tumor-free animals continued treatment until tumor formation. By day 18, 4/12 animals treated with MBP-vasostatin (Seq. I.D. No. 4) as opposed to 12/12 control-treated animals had developed a tumor (p=0.0013). The mean (±SD) weight of tumors in the untreated control group (0.43±0.2 g) was greater than the weight of tumors from vasostatin-treated animals (0.21±0.05 g), but the weight difference did not reach statistical significance (p=0.059). With continued MBP-vasostatin (Seq. I.D. No. 4) treatment, one additional tumor appeared on day 23, but the remaining 7 animals remain tumor-free as of day 60.

In an additional experiment (FIG. 3D), vasostatin (Seq. I.D. No. 4) was administered at a higher dose (100 μg/mouse, daily, 6 days/week) and compared it to a lower dose (20 μg/mouse, daily, 6 days/week). After 18 days of treatment, all mice (6/6) inoculated with formulation buffer alone had developed a tumor. By contrast, none of the mice (0/9) inoculated with MBP-vasostatin at the dose of 100 μg/mouse had developed a tumor (p=0.0002). In addition, 3/5 mice inoculated with MBP-vasostatin at the dose of 20 μg/mouse developed a tumor (not significantly different from control, p=0.018), indicating a dose effect. Treatment was continued unchanged until tumors appeared. As of day 30, only one tumor has appeared in the group treated with the highest dose.

Subsequent tests were done to determine the effect of vasostatin (Seq. I.D. No. 4) on established human Burkitt lymphoma. To this end, Burkitt tumors were first established in the animals and then treatment was initiated. As shown in FIG. 4A, the rate of Burkitt lymphoma growth was significantly reduced in the group (9 mice) treated with vasostatin (Seq. I.D. No. 4) at a dose 200 μg/mouse compared to the controls (10 mice) treated with formulation buffer alone or MBP (p=0.003). Tumors were removed on day 48. The mean weight of Burkitt tumors in the control group (6.89±2.6 g) was significantly greater (p=0.0005) than the mean weight of tumors treated with vasostatin (2.74±1.6 g). In an additional experiment, vasostatin (Seq. I.D. No. 4) was used at a higher dose (200 μg/twice/day, 5 days/week and once/day 2 days/week) for 38 days. As shown in FIG. 4B, vasostatin treatment promoted the disappearance of 4 out of 12 Burkitt tumors but, as expected, formulation buffer alone did not have this effect. After treatment was completed on day 38, all animals with tumor were sacrificed and tumor weight measured. The mean weight of Burkitt tumors in the control group (3.95±0.77 g) was significantly greater (p=0.014) than the mean weight of tumors treated with vasostatin (1.74±0.44 g; Seq. I.D. No. 4). All 4 mice treated with vasostatin (Seq. I.D. No. 4) and without a tumor on day 38 were observed without treatment. As of day 70, none of the tumors have reappeared. These experiments indicate that vasostatin can delay, prevent, or cure Burkitt tumor development in a murine model.

In an additional experiment, MBP-Δ120 calreticulin (30 μg/mouse; Seq. I.D. No. 9) was tested for its ability to prevent Burkitt tumor growth, and compared its effects to those of MBP-vasostatin (30 μm/mouse; Seq. I.D. No. 4). After 14 days of treatment, all mice (8/8) inoculated with control MBP (20 μg/mouse) developed a tumor. By contrast, only 3/9 mice inoculated with MBP-Δ120 calreticulin (Seq. I.D. No. 9), and 3/9 mice inoculated with MBP-vasostatin (Seq. I.D. No. 4) developed a tumor (p=0.009). After treatment was suspended on day 14, the mice were observed. One mouse from the group treated with MBP-Δ120 calreticulin (Seq. I.D. No. 9) and one mouse from the group treated with MBP-vasostatin (Seq. I.D. No. 4) remain tumor-free as of day 60. Thus, similar to vasostatin (Seq. I.D. No. 4), MBP-Δ120 calreticulin (Seq. I.D. No. 9) can prevent Burkitt tumor growth.

For histological examination, tumor plugs were fixed in 10% neutral buffered formalin solution (Sigma), embedded in paraffin, sectioned at 4 μm, and stained with hematoxylin and eosin, or Masson's trichrome by standard methods. Histology of tumors that emerged on calreticulin (Seq. I.D. No. 3) or vasostatin (Seq. I.D. No. 4) treatment showed subtle characteristic changes to the tumor vasculature, including intimal and medial thickening of the vessel wall. These alterations were absent from tumors of control animals. The tumor tissue from test and control animals was indistinguishable with respect to morphology of tumor cells and the number of mitoses. However, tumors from calreticulin and vasostatin-treated animals displayed occasional infiltration with neutrophils, histiocytes, and lymphocytes that were absent from control tumors. In addition, tumor tissues from animals treated with vasostatin or calreticulin displayed a significant reduction in the number of vessels identified by immunohistochemical staining for the endothelial cell marker CD31. No abnormalities were noted on gross and histological examination of liver, spleen, kidneys, heart, lung and lymph nodes from calreticulin and vasostatin-treated animals.

VII. Calreticulin Fragment Inhibits the Growth of Colon Carcinomas, Breast Adenocarcinomas and Neuroblastoma Tumors, Wilms Tumor, Rhabdomyosarcoma, Promyelomonocytic Lymphoma, Murine lymphoma, and Melanoma Tumors.

Figure 8:
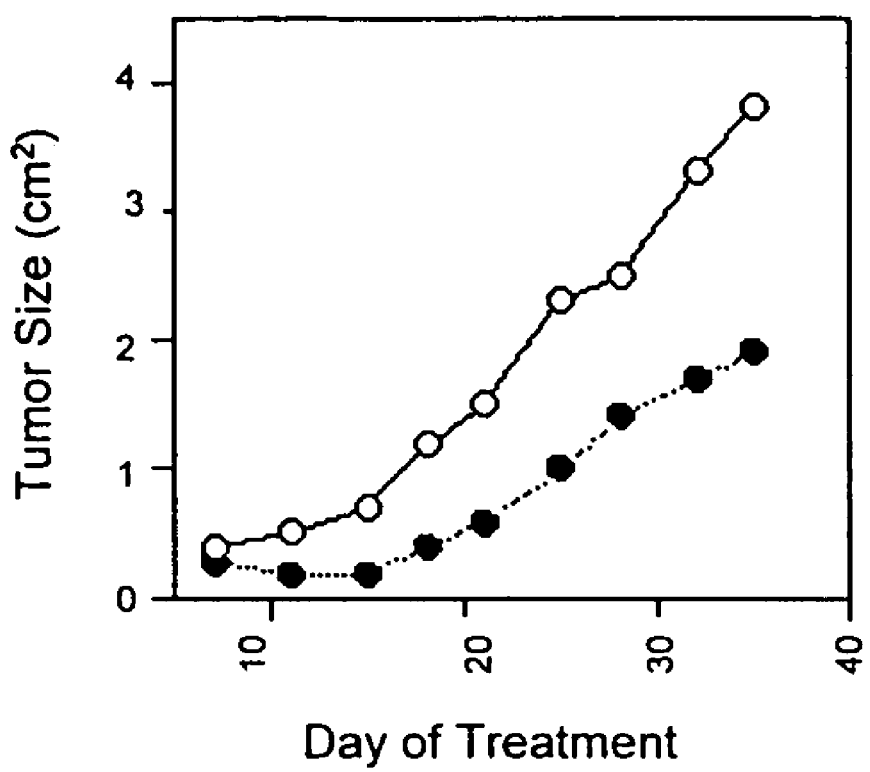
FIG. 8 is a graph showing the inhibition of human colon carcinoma growth by vasostatin (Seq. I.D. No. 4). Mice (BALB/c athymic mice, 6 weeks of age) were inoculated s.c. with the human colon carcinoma cell line (SW-480 from ATCC, 6×10$^6$ cells/mouse in 0.2 ml RPMI medium). After a tumor appeared (at least 130 mm$^2$ in size), 12 mice were treated with MBP-vasostatin (100 μg/day, 6 days/week, 100 μl/dose, ×36 days; closed circles; (Seq. I.D. No. 4) and 10 mice were inoculated with formulation buffer (100 μl×36 days; open circles). Tumor size was estimated as the product of two-dimensional caliper measurements.

Additional experiments were designed to test the effect of vasostatin treatment on human colon carcinoma established in athymic mice. To this end, BALB/c athymic mice were inoculated s.c. with the cells of the human colon carcinoma SW-480 cell line. After a tumor appeared (at least 130 mm² in size), 12 mice were treated s.c. with vasostatin and 10 mice were similarly treated with formulation buffer. Tumor growth was significantly reduced in the group treated with vasostatin at a dose of 100 μg/mouse (12 mice) compared to the control group (10 mice) treated with formulation buffer alone (p=0.0003, FIG. 8). All tumors were removed on day 39 of treatment. The mean (±SD) weight of colon carcinoma tumors in the control group (3.04±0.6 g) was significantly (p=0.0004) greater than the weight of tumors from vasostatin-treated animals (1.48±0.64 g).

Figure 9A:
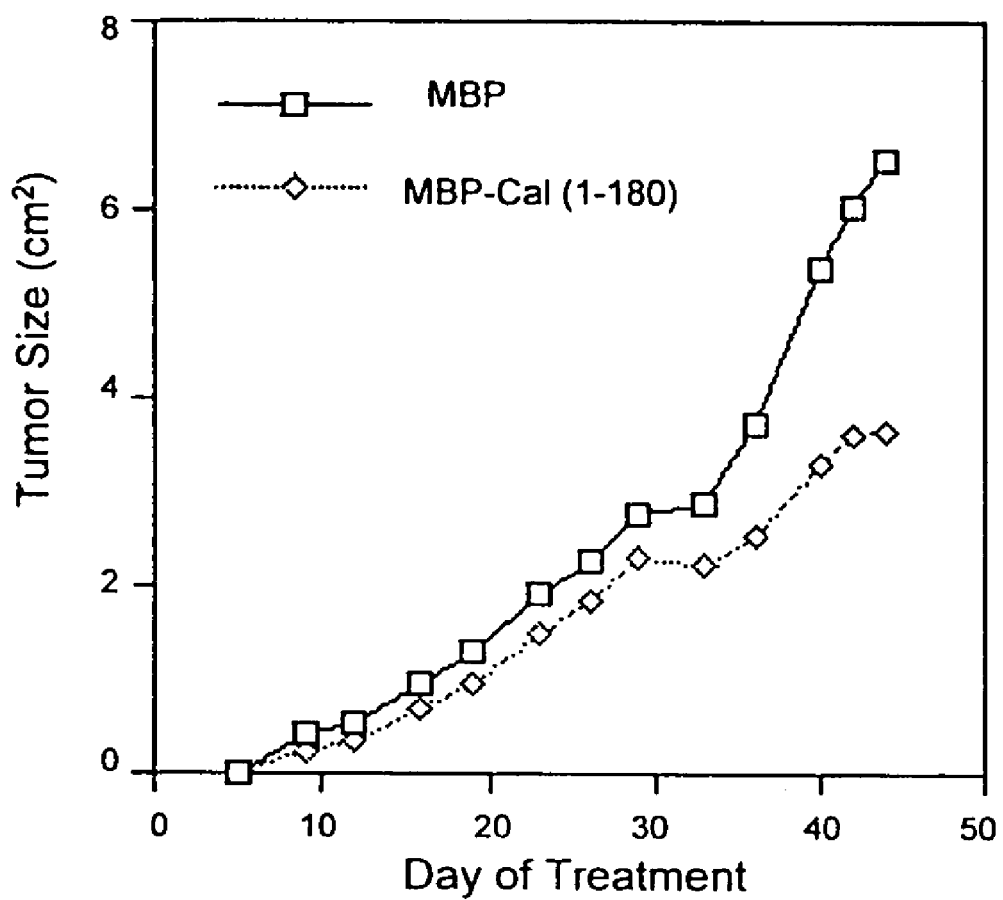
FIGS. 9A and 9B are graphs showing the inhibition of human neuroblastoma tumor growth. Mice (BALB/c athymic mice, 6 weeks of age) were inoculated s.c. with the human neuroblastoma cell line (SK-N-MC from ATCC, 8.5×10$^6$ cells/mouse in 0.2 ml RPMI medium). Beginning on the day of cell inoculation and continuing thereafter daily, 6 days/week, 12 mice were inoculated s.c. with control MBP (20 μg/day) and 13 mice were inoculated with MBP-vasostatin (30 μg/day). On day 30, 8 of the 12 mice that had been injected with control MBP (mean tumor weight 1.74 g) and 5 of the 13 mice injected with MBP-vasostatin (Seq. I.D. No. 4; mean tumor weight 1.78 g) were sacrificed. Treatment was continued in the remaining mice until day 55 at which time all animals were sacrificed. One of the mice treated with MBP-vasostatin (Seq. I.D. No. 4) did not develop a tumor and since day 55 was observed untreated; as of day 220 no tumor has developed. On day 55, all animals with tumor were sacrificed and tumor weight measured. There were 4 animals in the control group (MBP) and 7 animals in the treatment group (MBP-vasostatin). A. Tumor growth curves. B. Comparison of tumor weights in animals sacrificed on day 55.
Figure 9B:
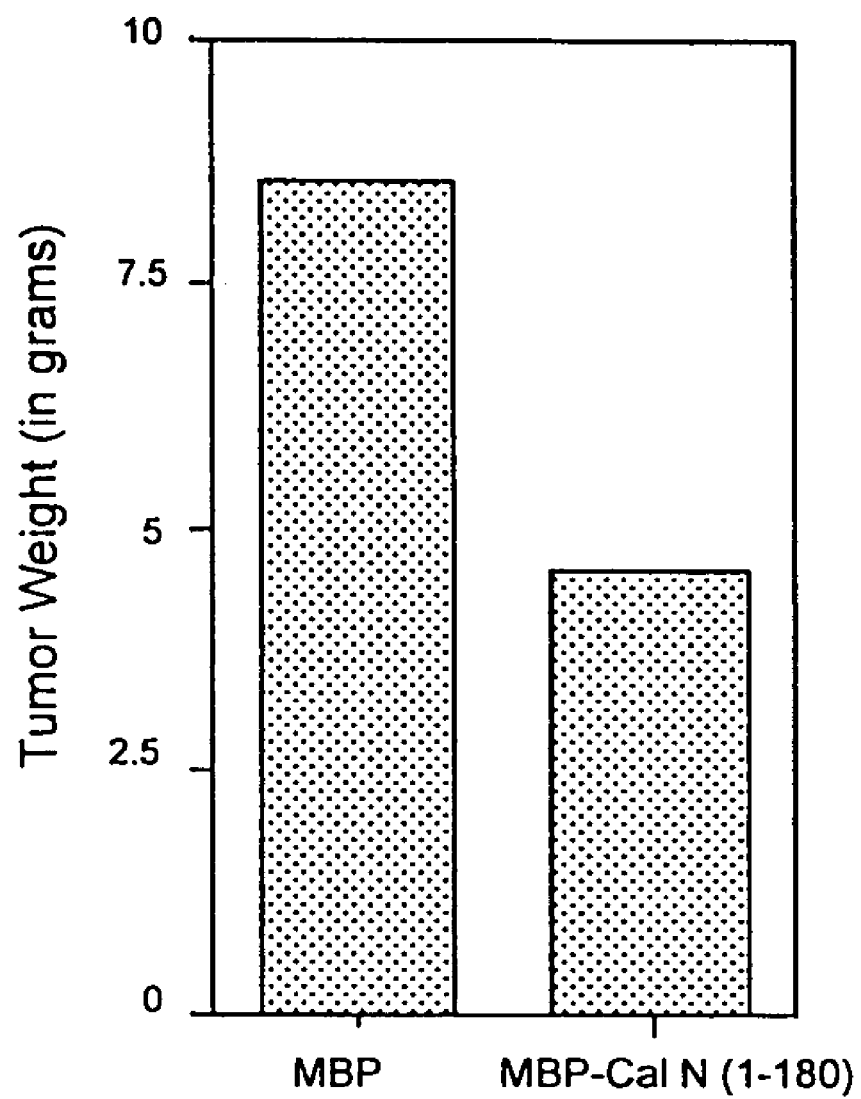

The effects of vasostatin on human neuroblastoma tumor growth in athymic mice were also tested. To this end, athymic BALB/c mice were inoculated s.c. with the human neuroblastoma SK-N-MC cell line. Beginning on the day of cell inoculation and continuing thereafter daily, the mice received s.c. either control MBP (20 µg/day) or MBP-vasostatin (30 µg/day; (Seq. I.D. No. 4). On day 30, 8 of the 12 mice receiving control MBP (mean tumor weight 1.74 g) and 5 of the 12 mice receiving MBP-vasostatin (mean tumor weight 1.78 g; Seq. I.D. No. 4) were sacrificed. Treatment was continued unchanged in the remaining animals until day 55 at which time all animals with tumor were sacrificed. One of the 12 mice treated with MBP-vasostatin (Seq. I.D. No. 4) never developed a tumor and remains tumor-free without treatment as of day 220. As shown (FIGS. 9A and 9B), the rate of tumor growth was reduced in the mice treated with vasostatin (p=0.07). In addition, the mean (±SD) weight of neuroblastoma tumors removed on day 55 in the control group (8.579±1.21) was greater than the weight of tumors from vasostatin-treated animals (4.58±0.64 g).

Figure 10:
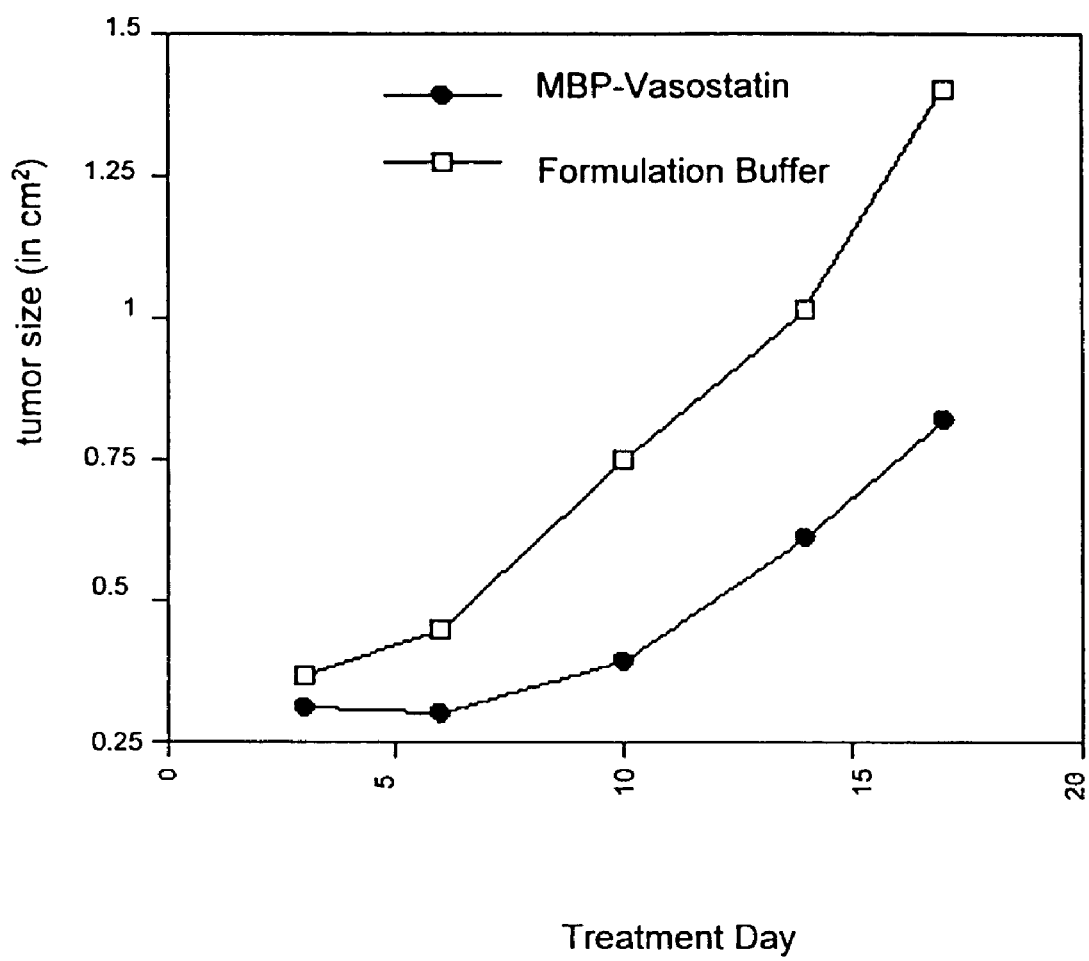
FIG. 10 is a graph showing the inhibition of human breast adenocarcinoma tumor growth by vasostatin (Seq. I.D. No. 4). Mice (BALB/c athymic mice, 6 weeks of age) were inoculated s.c. with the human breast adenocarcinoma cell line (MDA-MB231 from ATCC, 7.5×10$^6$ cells/mouse in 0.2 ml RPMI medium). Beginning on the day of cell inoculation and continuing thereafter daily, 5 days/week, for 18 days, 8 mice were inoculated s.c. with control formulation buffer (100 μl/injection/twice/day for 5 days/week and once/day for 2 days/week) and 8 mice were inoculated with MBP-vasostatin (Seq. I.D. No. 4; 200 μg/twice/day for 5 days/week and once/day for 2 days/week). Tumor size was estimated as the product of two-dimensional caliper measurements.

Furthermore, the effect of vasostatin (Seq. I.D. No. 4) on human breast adenocarcinoma growth in athymic mice was also tested (FIG. 10). Athymic BALB/c nude mice were inoculated s.c. with the human breast adenocarcinoma cell line MDA-MB231. Beginning on the day of cell inoculation and continuing daily thereafter (5 days/week for 18 days) the mice were inoculated s.c. with either MBP vasostatin (200 µg/day, 5 days/week and 100 µg/day 2 days week; Seq. I.D. No. 4) or formulation buffer control. As shown, breast adenocarcinoma tumor growth was reduced by MBP-vasostatin. There was no evidence of local or systemic toxicity in vasostatin-treated animals.

To establish whether vasostatin could inhibit tumor growth in a syngeneic system, BALB/c nude mice were injected s.c. with the murine B-cell lymphoma cell line Raw 8.1 (also BALB/c). Beginning on the day of cell inoculation and continuing thereafter daily, 9 mice were inoculated s.c. with control formulation buffer and 9 mice were treated with MBP-vasostatin (200 µg/day; Seq. I.D. No. 4).

Figure 11A:
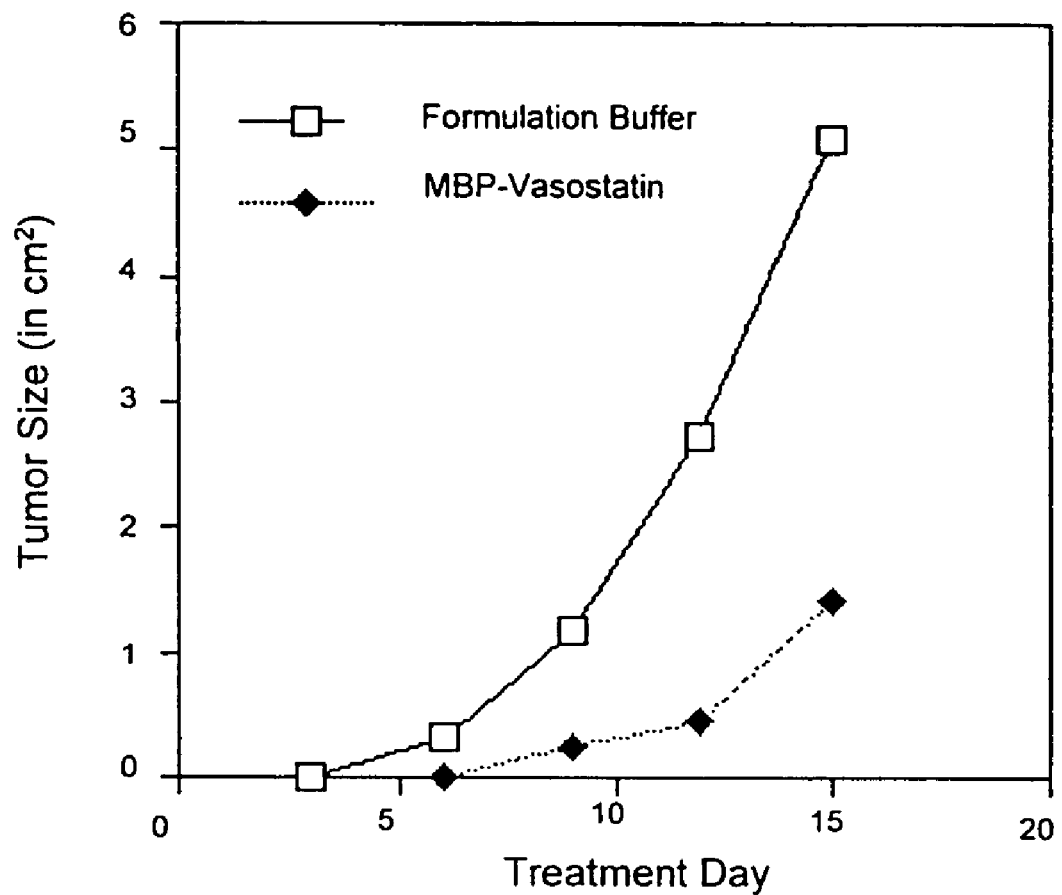
FIGS. 11A and 11B are graphs showing the inhibition of murine lymphoma tumor growth by vasostatin (Seq. I.D. No. 4). Mice (BALB/c athymic mice, 6 weeks of age) were inoculated s.c. with the murine B-cell lymphoma cell line (Raw 8.1 from ATCC, 2.5×10$^6$ cells/mouse in 0.2 ml RPMI medium). Beginning on the day of cell inoculation and continuing thereafter daily, 7 days/week, 9 mice were inoculated s.c. with control formulation buffer (100 μl/day) and 9 mice were inoculated with MBP-vasostatin (Seq. I.D. No. 4; 200 μg/day). Treatment was continued until all mice developed a tumor measuring at least 0.5 cm$^2$ on day 15. A. Tumor size, estimated as the product of two-dimensional caliper measurements, was recorded for control and vasostatin-treated mice. B. Tumor weight in control and vasostatin treated mice measured on day 15.
Figure 11B:
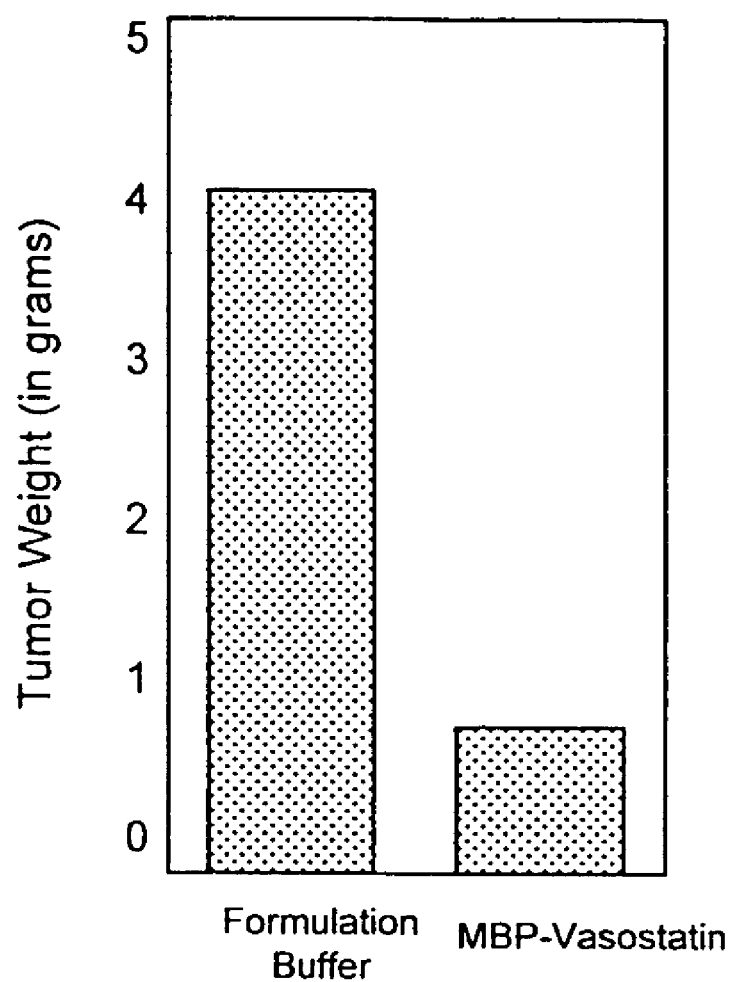

Treatment was stopped when all animals developed a tumor on day 15. As shown (FIG. 11A) vasostatin treatment reduced significantly murine lymphoma tumor growth (p<0.01). In addition (FIG. 11B), the mean (±SD) weight of the tumors in the control group (4.51±0.8 g) was significantly (p<0.01) greater than the weight of tumors from vasostatin-treated animals (0.86±0.34 g). These experiments demonstrate that vasostatin (Seq. I.D. No. 4) exhibits a potent anti-tumor effect not only in athymic mice bearing xenogeneic tumors, but also in athymic mice bearing syngeneic tumors.

Figure 12:
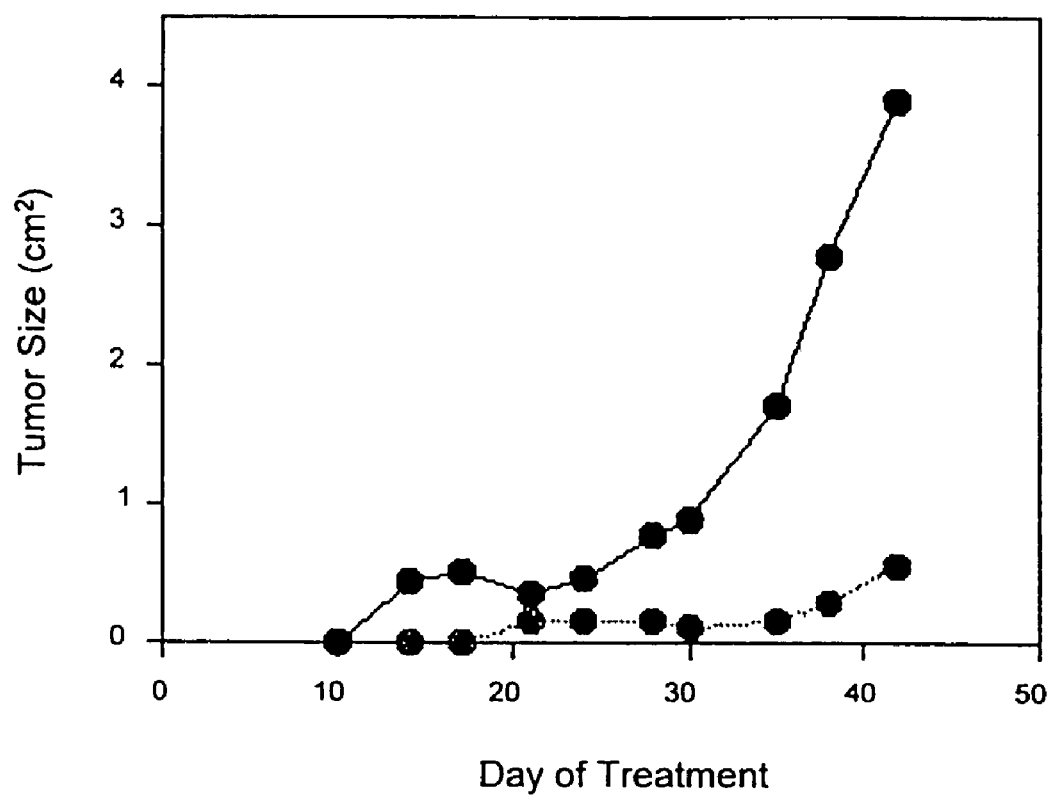
FIG. 12 is a graph showing the inhibition of Wilms tumor growth by vasostatin (Seq. I.D. No. 4). Athymic BALB/c nude mice received 400 rad total body irradiation and 24 hours later were inoculated (12×10$^6$ cell/mouse) with the human Wilms tumor cell line (SK-NP-1). One day after cell injection, and continuing daily thereafter for 42 days, the mice received either control formulation buffer alone or MBP-vasostatin (Seq. I.D. No. 4; 100 μg/day, 6 days/week). Tumor size was estimated as the product of two dimesional caliper measurement.

Additional tests measuring the effects of vasostatin (Seq. I.D. No. 4) on Wilms tumors were done (FIG. 12). Athymic BALB/c nude mice received 400 rad total body irradiation and 24 hours later were inoculated (12×10$^6$ cell/mouse) with the human Wilms tumor cell line (SK-NP-1). One day after cell injection, and continuing daily thereafter for 42 days, the mice received either control formulation buffer alone or MBP-vasostatin (100 µg/day, 6 days/week; Seq. I.D. No. 4). As shown, MBP-vasostatin (Seq. I.D. No. 4) induced a significant reduction of Wilms tumor growth (p=0.0082).

Figure 13:
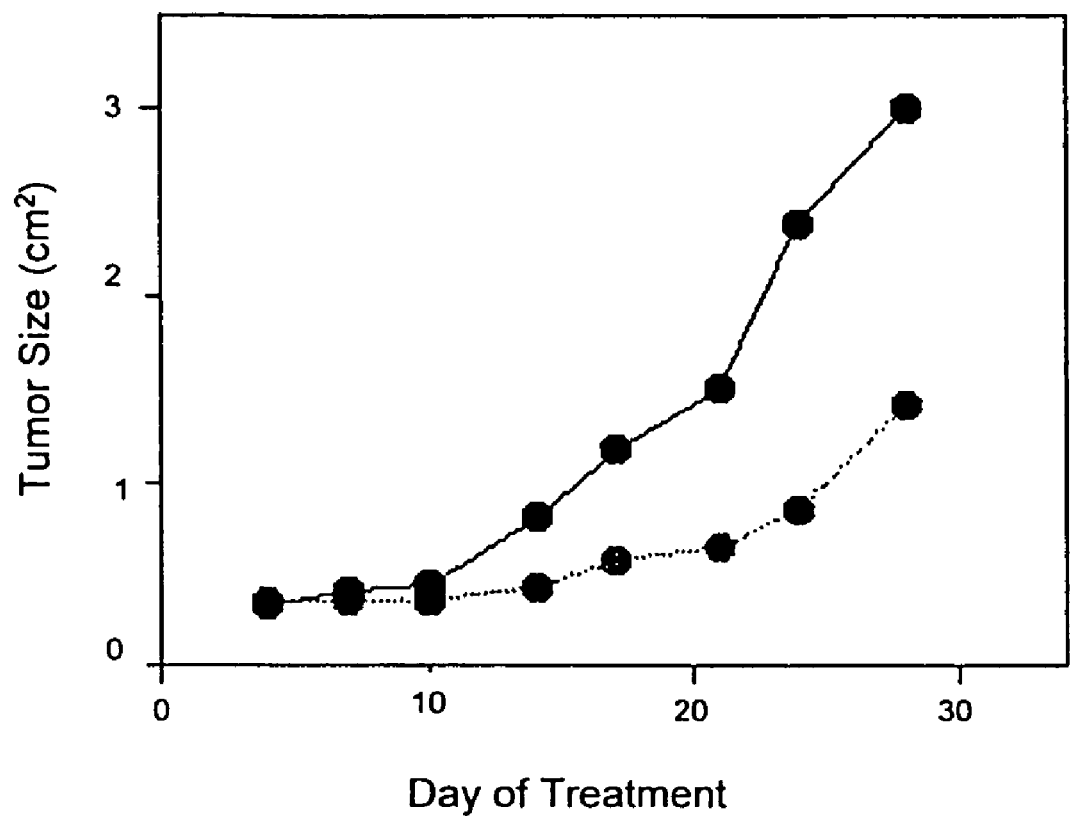
FIG. 13 is a graph showing the inhibition of rhabdomyosarcoma growth by vasostatin (Seq. I.D. No. 4). Groups of athymic BALB/c nude mice received 400 rad total body irradiation and 24 hours later were inoculated ($8 \times 10^6$ cell/mouse) s.c. with the human rhabdomyosarcoma cell line A-204 tumor cell line (SK-NP-1). One day after cell injection, and continuing daily thereafter for 28 days, the mice received either control formulation buffer alone or MBP-vasostatin (Seq. I.D. No. 4; 100 μg/day, 6 days/week). Tumor size was estimated as the product of two dimesional caliper measurement.

The effects of MBP-vasostatin treatment on the human rhabdomyosarcoma cell line A-204 injected into nude mice were examined (FIG. 13). Groups of athymic BALB/c nude mice received 400 rad total body irradiation and 24 hours later were inoculated (8×10$^6$ cell/mouse) s.c. with the human rhabdomyosarcoma cell line A-204. One day after cell injection, and continuing daily thereafter for 28 days, the mice received either control formulation buffer alone or MBP-vasostatin (100 µg/day, 6 days/week; Seq. I.D. No. 4). As shown, MBP-vasostatin reduced significantly the rate of growth of rhabdomyosarcoma in the mice (p=0.0006). The mean tumor weight in the control group (2.449 g) was significantly greater (p=0.0009) than the mean tumor weight in the treated group (0.859 g).

Figure 14:
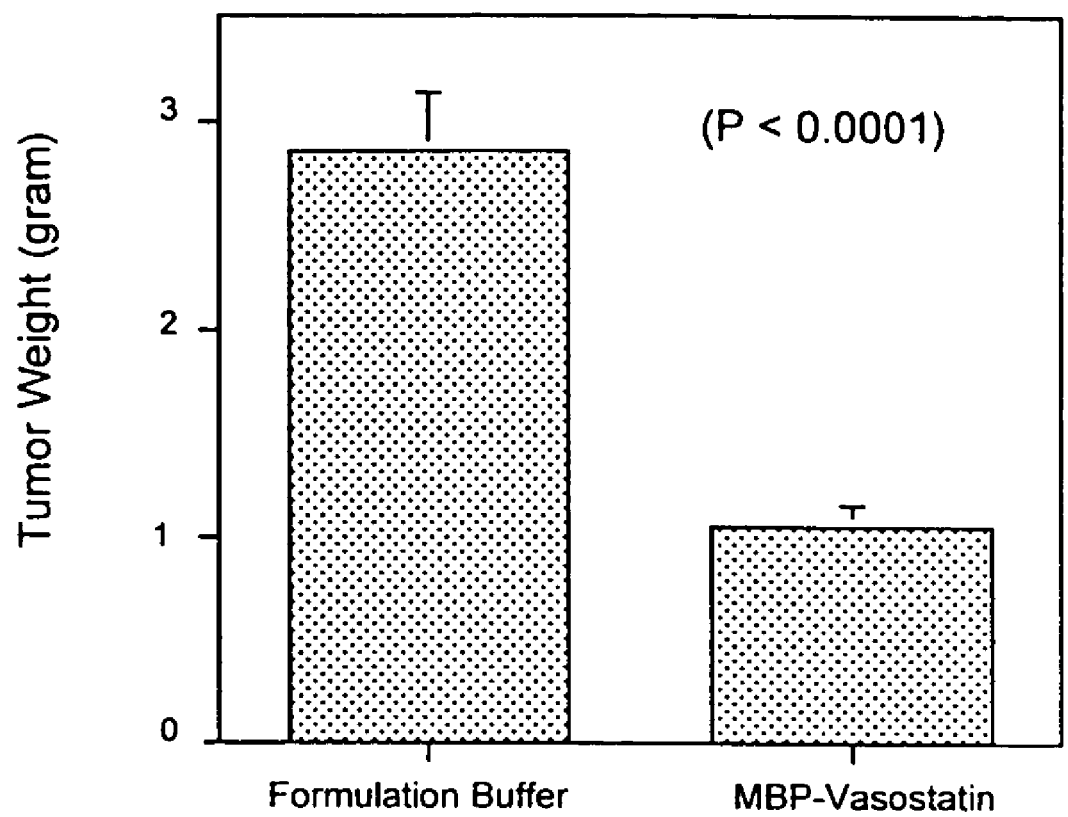
FIG. 14 is a bar graph showing the inhibition of myelomonocytic lymphoma growth by vasostatin (Seq. I.D. No. 4). Groups of athymic BALB/c nude mice received 400 rad total body irradiation and 24 hours later were inoculated ($10 \times 10^6$ cell/mouse) with the human HL60 tumor cell line. One day after cell injection, and continuing daily thereafter for 24 days, the mice received either control formulation buffer alone or MBP-vasostatin (Seq. I.D. No. 4; 200 μg/day, 6 days/week). The weight of each tumor was measured in grams after tumors were removed from the animals.

MBP-vasostatin (Seq. I.D. No. 4) was tested for its ability to reduce the growth of the human promyelomonocytic cell line HL60 inoculated s.c. into nude mice (FIG. 14). Groups of athymic BALB/c nude mice received 400 rad total body irradiation and 24 hours later were inoculated (10×10$^6$ cell/mouse) with the human promyelomonocytic cell line HL60. One day after cell injection, and continuing daily thereafter for 24 days, the mice received either control formulation buffer alone or MBP-vasostatin (200 µg/day, 6 days/week; Seq. I.D. No. 4). The rate of tumor growth was significantly greater in the control group as compared to the treated group (p<0.001). As shown, mice treated with MBP-vasostatin (Seq. I.D. No. 4) were significantly smaller than the mice treated with formulation buffer (p<0.001).

Figure 15:
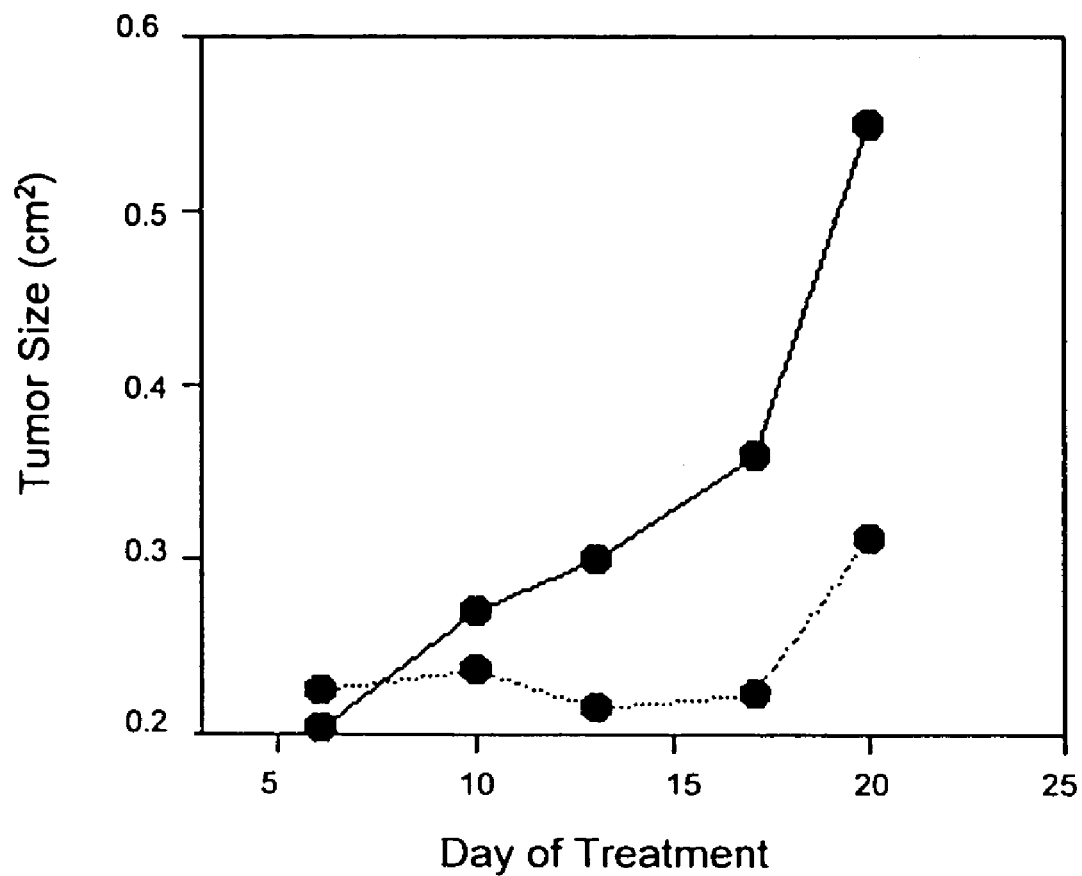
FIG. 15 is a graph showing the inhibition of human melanoma tumor growth by vasostatin (Seq. I.D. No. 4). Athymic BALB/c nude mice received 400 rad total body irradiation and 24 hours later were inoculated ($7 \times 10^6$ cell/mouse) with the human melanoma cell line (A-375). Five days after cell injection, and continuing daily thereafter for 20 days, the mice received either control formulation buffer alone or MBP-vasostatin (Seq. I.D. No. 4; 200 μg/day, 6 days/week). Tumor size was estimated as the product of two dimesional caliper measurement.

The effect of MBP-vasostatin (Seq. I.D. No. 4) on human melanoma tumors transplanted into nude mice was also tested (FIG. 15). Athymic BALB/c nude mice received 400 rad total body irradiation and 24 hours later were inoculated (7×10$^6$ cell/mouse) with the human melanoma cell line (A-375). Five days after cell injection, and continuing daily thereafter for 20 days, the mice received either control formulation buffer alone or MBP-vasostatin (200 µg/day, 6 days/week; Seq. I.D. No. 4). As shown, MBP-vasostatin induced a significant reduction of Wilms tumor growth (p=0.0059).

These experiments indicate that the N-terminal 180 amino acid fragment of calreticulin, vasostatin (Seq. I.D. No. 4), can delay or prevent the growth of human tumors of various lineages established in nude mice.

Figure 16:
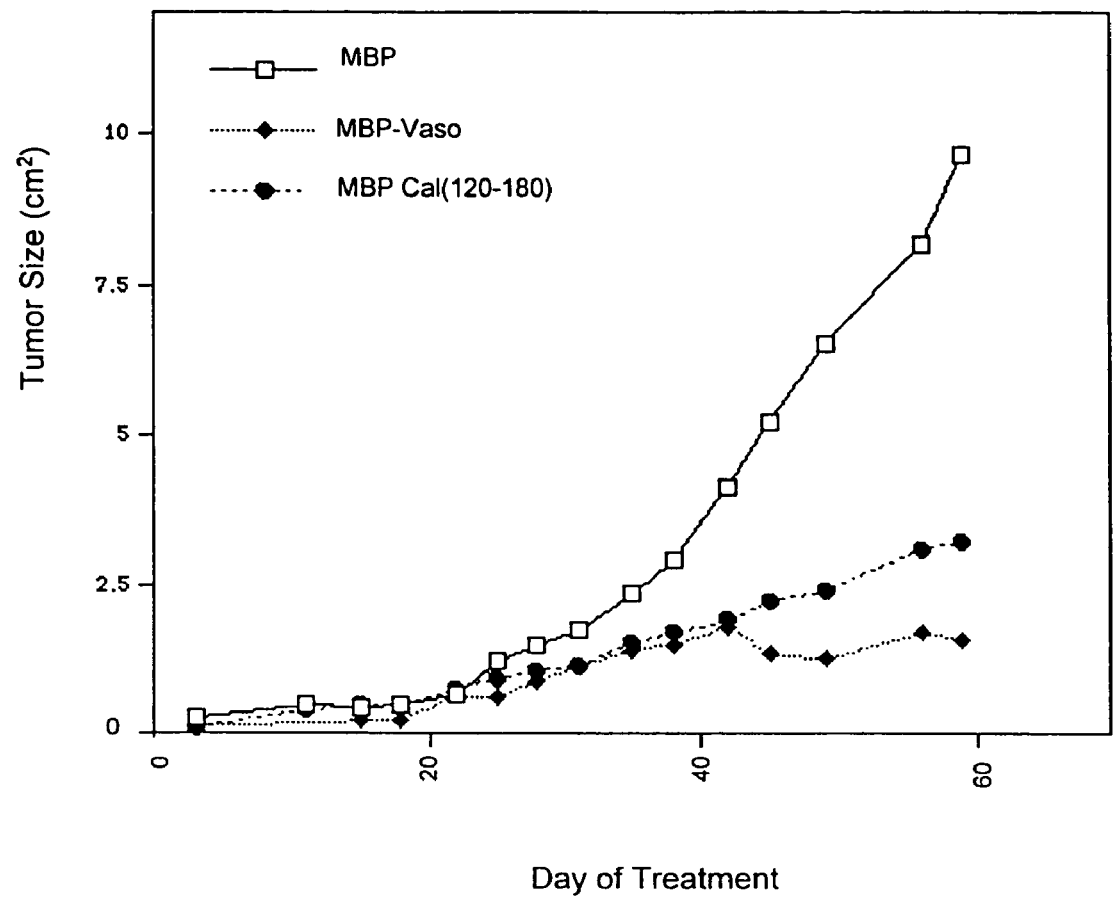
FIG. 16 is a graph showing the inhibition of human Burkitt lymphoma growth by the calreticulin fragment encompassing amino acids 120-180 (Seq. I.D. No. 5). Athymic BALB/c nude mice received 400 rad total body irradiation and 24 hours later were inoculated ($4 \times 10^6$ cell/mouse) with the human Burkitt lymphoma cell line CA46. Beginning on the day of cell inoculation and continuing daily thereafter 6 days/week the mice received either control recombinant purified MBP (65 μg/day, 6 days/week), MBP-vasostatin (Seq. I.D. No. 4; 100 μg/day, 6 days/week), or MBP-120-180 calreticulin (Seq. I.D. No. 5; 75 μg/day, 6 days/week). Mice were injected for 42 days. Tumor size was estimated as the product of two dimesional caliper measurement.
Figure 17A:
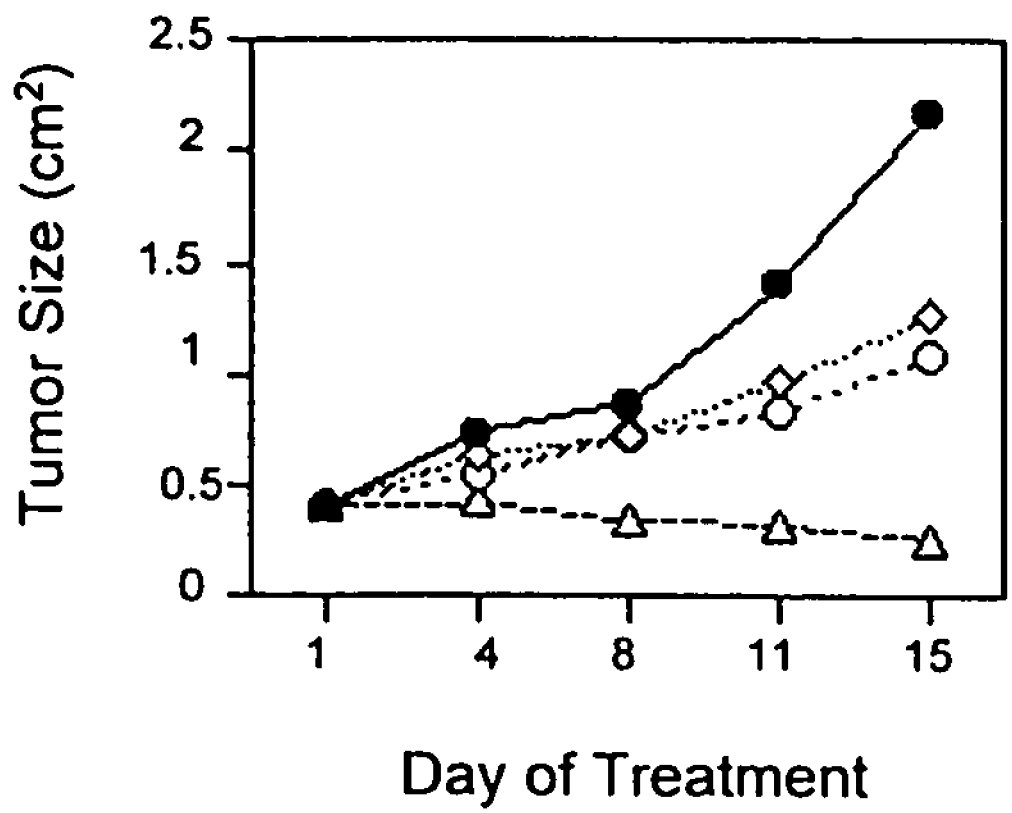
FIGS. 17A, 17B, 17C, and 17D are graphs showing the inhibition of human Burkitt lymphoma growth by a combination treatment of vasostatin (Seq. I.D. No. 4) and Interleukin 12 (IL-12). Athymic BALB/c nude mice received 400 rad total body irradiation and 24 hours later were inoculated ($4 \times 10^6$ cell/mouse) with the human Burkitt lymphoma cell line CA46. A and B. 5 days after cell inoculation the established tumors were treated with daily s.c. inoculations (6 days/week) of either formulation buffer alone (closed circles), vasostatin alone (Seq. I.D. No. 4; 100 μg/day; open squares), mIL-12 alone (200 ng/day for 8 days followed by 100 ng/day; open circles), or the combination of vasostatin (Seq. I.D. No. 4) and mIL-12 (same dose used as single agents; open triangles). All mice were sacrificed after 15 days of treatment. C and D. I day after cell inoculation, s.c. treatment with vasostatin (Seq. I.D. No. 4; 100 μg/day; 6 days/week) or formulation buffer was started; s.c. treatment with IL-12 (100 ng/mouse; 6 days/week) was started 2 days later in mice that had received buffer alone or vasostatin (Seq. I.D. No. 4). Therefore, four groups of mice were tested: Mice receiving buffer alone (closed circles); vasostatin alone (open squares); IL-12 alone (open circles); and vasostatin plus IL-12 (open triangles). The mice received 7 days treatment with vasostatin (Seq. I.D. No. 4) and 5 days treatment with IL-12, and were observed untreated for 14 days at which time all mice were sacrificed. Tumor size was estimated as the product of two-dimesional caliper measurement.
Figure 17B:
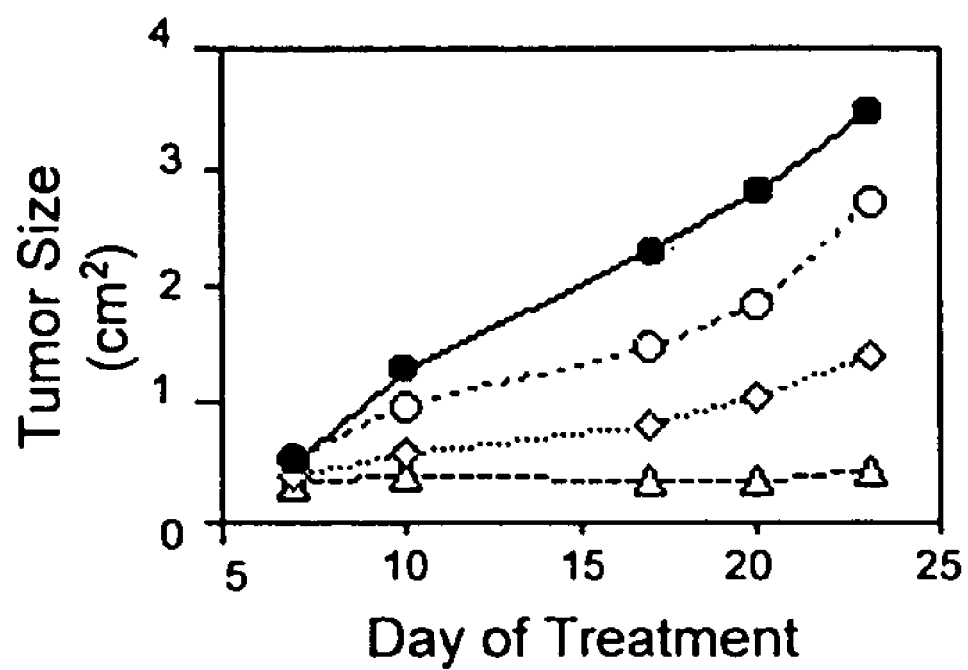
Figure 17C:
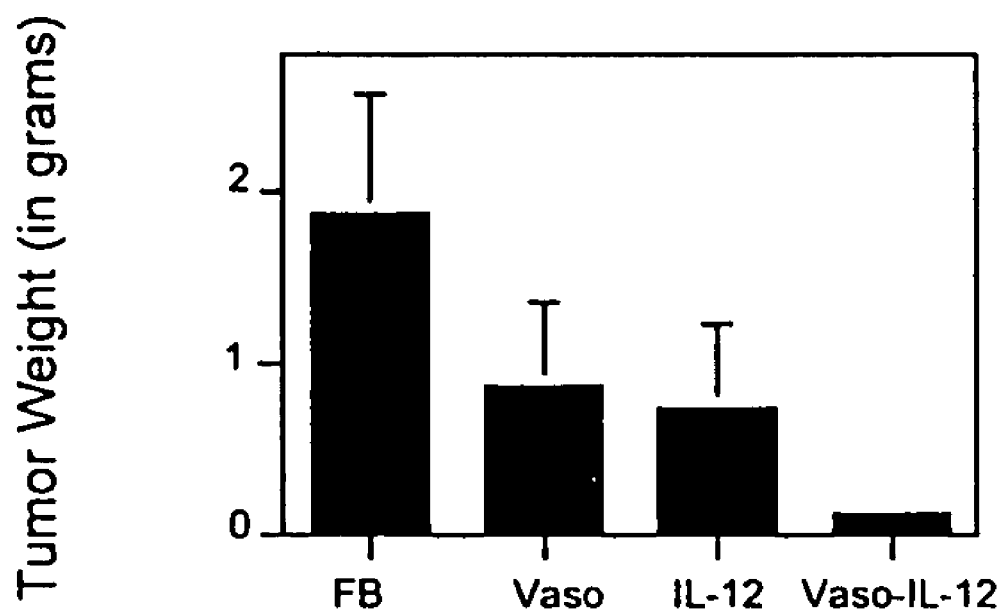
Figure 17D:
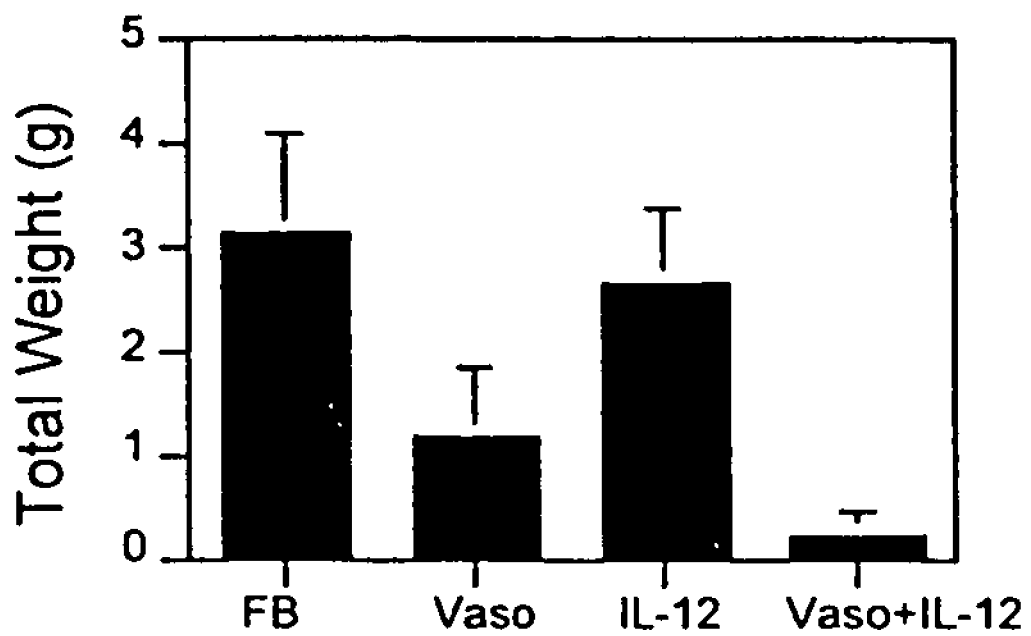

VIII. A 61 Amino Acid Fragment of Calreticulin (Amino Acids 120-180; Seq. I.D. No. 5) Inhibits Tumor Growth In Vivo In additional experiments, the 61 amino acid fragment of calreticulin encompassing amino acids 120-180 (Seq. I.D. No. 5) was tested for its ability to inhibit tumor growth. As described above, this calreticulin fragment was active in vivo as an inhibitor of tumor growth and was active in vivo as an inhibitor of angiogenesis. To this end, groups of athymic mice were irradiated with 400 rad, and 24 hours later were injected s.c. with 4×10$^6$ cells from the Burkitt lymphoma cell line CA46. Beginning on the day of cell inoculation and continuing daily thereafter 6 days/week the mice received either control recombinant purified MBP (65 µg/day, 6 days/week), MBP-vasostatin (100 µg/day, 6 days/week; Seq. I.D. No. 4), or MBP-120-180 calreticulin (75 µg/day, 6 days/week; Seq. I.D. No. 5). Mice were injected for 42 days. As shown (FIG. 16), the rate of tumor growth in the group of mice treated with MBP-vasostatin (Seq. I.D. No. 4) was significantly reduced when compared to controls (p=0.0122). In addition, the rate of tumor growth in the group of mice treated with MBP-120-180 calreticulin fragment (Seq. I.D. No. 5) was significantly reduced when compared to controls (p=0.0058). However, the rate of tumor growth in mice treated with MBP-vasostatin (Seq. I.D. No. 4) was not significantly different from the rate of tumor growth in the mice treated with the MBP-120-180 calreticulin fragment (p=0.74; Seq. I.D. No. 4). Hence, the calreticulin fragment (Seq. I.D. No. 4) is active as an inhibitor of tumor growth in vivo.

IX. Antitumor Effects of Combination Therapy with Vasostatin and Interleukin-12

The effects of vasostatin and murine IL-12 (mIL-12), alone and together, were tested on human Burkitt lymphoma established in nude mice (FIG. 17). In the first experiment (FIG. 17A), the Burkitt cell line CA46 was inoculated s.c. into athymic mice, and 5 days later the established tumors were treated with daily s.c. inoculations (6 days/week) of either formulation buffer alone, vasostatin alone (100 µg/day; Seq. I.D. No. 4), mIL-12 alone (200 ng/day for 8 days followed by 100 ng/day), or the combination of vasostatin (Seq. I.D. No. 4) and mIL-12 (same dose used as single agents). All mice were sacrificed after 15 days of treatment. In a second experiment (FIG. 17B), s.c. treatment with vasostatin (100 µg/day; 6 days/week; Seq. I.D. No. 4) or formulation buffer was started one day after the Burkitt Ca46 cells were injected into the nude mice, and s.c. treatment with IL-12 (100 ng/mouse; 6 days/week) was started 2 days later in mice that had received buffer alone or vasostatin (Seq. I.D. No. 4). The mice received 7 days treatment with vasostatin (Seq. I.D. No. 4) and 5 days treatment with IL-12, and were observed untreated for 14 days at which time all mice were sacrificed. The delayed addition of IL-12 and the shorter duration of IL-12 treatment in the second experiment resulted in IL-12 having a somewhat reduced effect on tumor growth and weight compared to the first experiment (FIGS. 17A and 17B). However, in both experiments the rate of tumor growth and the mean weight of tumors was reduced by treatment with vasostatin (Seq. I.D. No. 4), mIL-12, or the combination of vasostatin (Seq. I.D. No. 4) plus mIL-12 compared with the control group treated with formulation buffer. Furthermore, the combination of IL-12 and vasostatin (Seq. I.D. No. 4) was more effective than either IL-12 alone (p=0.018 and p<0.0001, FIGS. 17A and 17B respectively) or vasostatin (Seq. I.D. No. 4) alone (p=0.0029 and p=0.0046, FIGS. 1A and 1B, respectively) at reducing the rate of tumor growth.

X. Therapeutic Activity does not Stem from Binding to the Amino Acid Sequence $KXaa_1FFXaa_2R$ (Seq. I.D. No. 11), or $KXaa_1GFFKR$ (Seq. I.D. No. 10)

Attempts to identify a putative receptor for calreticulin and active calreticulin fragments on endothelial cells have focused initially on the possibility that such receptor might share the sequence motif $KXaa_1FFXaa_2R$ (Seq. I.D. No. 11) present on distinct proteins known to bind calreticulin (Michalak et al. *Biochem. J.* 285:681-692, 1992; Coppolino et al., *Nature* 386:843-847, 1997; Coppolino et al., *J. Biol. Chem.* 270:23132-23138, 1995; Dedhar et al., *Nature* 367: 480-483, 1994). Proteins known to bind calreticulin through a virtually identical amino acid sequence motif include the cytoplasmic domain of the alpha subunit of integrins ($KXaa_1GFFKR$; Seq. I.D. No. 10) and a family of steroid receptors ($KXaa_1FFXaa_2R$; Seq. I.D. No. 11). Specific examples of integrin amino acid sequences and steroid receptor sequences are provided in Table 5.

TABLE 5

Conservation of an Amino Acid Sequence Motif in the Integrin Alpha-subunit Cytoplasmic Domains and in the Steroid Hormone Receptor Family (Table derived from U.S. Pat. No. 5,854,202 to Dedhar)

| Integrins | | | | Steroid Nuclear Receptors | | | |
|---|---|---|---|---|---|---|---|
| consensus sequence | $KX_{aa1}GFFKR$ | Seq. ID No. 10 | | consensus sequence | $KX_{aa1}FFX_{aa2}R$ | Seq. ID No. 11 | |
| a1 | KIGFFKR | Seq. ID No. 12 | | RARa | *ACEGCKGFFRRSVQK | Seq. ID No. 21 | |
| a2 | KLGFFKR | Seq. ID No. 13 | | T$_3$Rb | TCEGCKGFFRRTIQK | Seq. ID No. 22 | |
| a3 | KGGFFKR | Seq. ID No. 14 | | VDR | TCEGCKGFFRRSMKR | Seq. ID No. 23 | |
| a4 | KAGFFKR | Seq. ID No. 15 | | GR | TCGSCKVFFKRAVEG | Seq. ID No. 24 | |
| a5 | KLGFFKR | Seq. ID No. 13 | | MR | TCGSCKVFFKRAVEG | Seq. ID No. 24 | |
| a6(A) | KCGFFKR | Seq. ID No. 17 | | AR | *TCGSCKVFFKRAAEK | Seq. ID No. 25 | |
| a6(B) | KCGFFKR | Seq. ID No. 16 | | PR | TCGSCKVFFKRAMEG | Seq. ID No. 26 | |
| a7 | KLGFFKR | Seq. ID No. 13 | | ER | SCEGCKAFFKRSIQG | Seq. ID No. 27 | |
| a8 (chick) | KCGFFDR | Seq. ID No. 17 | | RXR | SCEGCKGFFKRTVRK | Seq. ID No. 28 | |
| av | RMGFFKR | Seq. ID No. 18 | | Steroid Receptor TR2 | TCEGCTGFFKRSIRK | Seq. ID No. 29 | |
| Mac-1 | KLGFFKR | Seq. ID No. 13 | | Nerve growth factor induced protein 1-B | TCEGCKGFFKRTVQK | Seq. ID No. 30 | |
| p150 | KVGFFKR | Seq. ID No. 19 | | Early response protein NAK1 | TCEGCKGFFKRTVQK | Seq. ID No. 30 | |
| PS2 (Drosophila) | KCGFFNR | Seq. ID No. 20 | | Chorion Factor 1 | SCEGCKGFFKRTVRK | Seq. ID No. 31 | |

*Sequences modified to conform to currently available sequence information.

To address this possibility, natural calreticulin fragments (purified from the culture supernatant of the VDS-O cell line) which were biologically active as inhibitors of endothelial cell growth were tested to determine if they were capable of binding to amino acid sequences from the steroid nuclear receptor and the cytoplasmic domain of alpha integrin. If binding to these sequences is critical to the endothelial cell inhibitory function of calreticulin and its fragments, it should be possible to remove the biologically active molecules through affinity binding.

Figure 18:
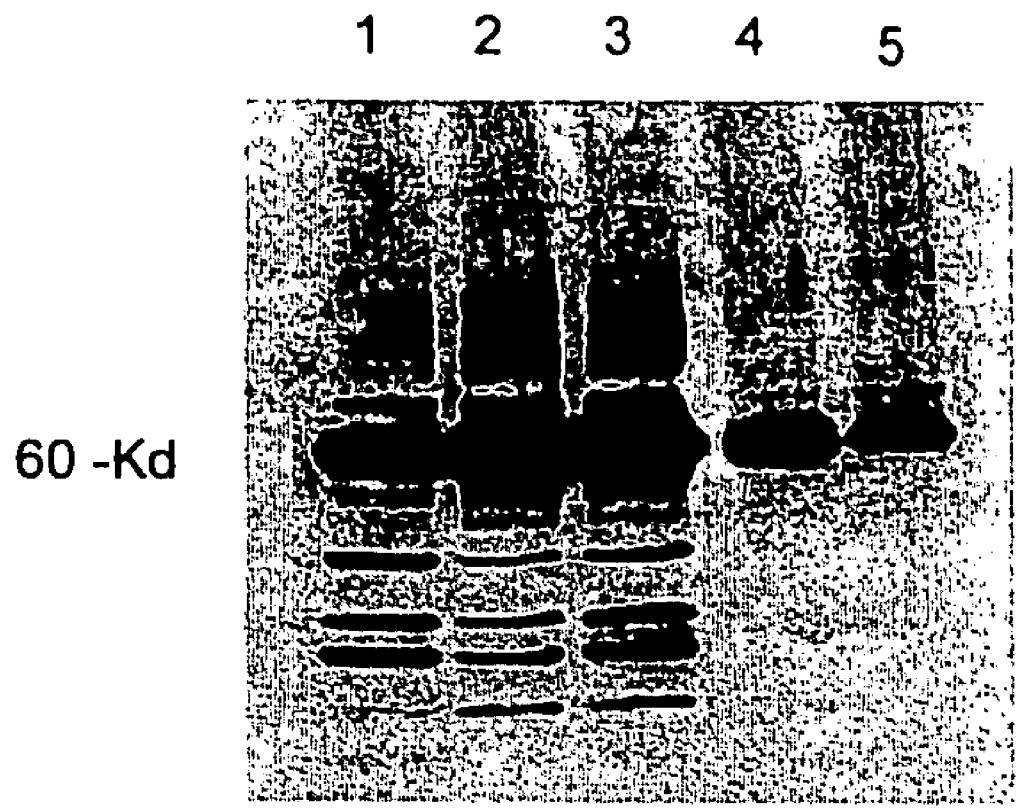
FIG. 18 is a Western blot analysis of fractions obtained through affinity purification over a column containing KXaa$_1$FFXaa$_2$R (Seq. I.D. No. 11) and KXaa$_1$GFFKR (Seq. I.D. No. 10). Purified supernatants from the VDS-0 cell line containing full length calreticulin and N-terminal fragments of calreticulin were affinity purified over a mixture of peptides KLGFFKR (Seq. I.D. No. 13), KAFFKR (Seq. I.D. No. 33) and KVFFKR (Seq. I.D. No. 32) coupled to CNBr-activated Sepharose. Starting material (lane 1), unbound material (lanes 2, 3) and bound material (lanes 4, 5) were separated by SDS-PAGE, transferred to nitrocellulose, and subsequently stained with a rabbit antiserum against human calreticulin.

To this end, purified preparations of the VDS-O cell line containing full length calreticulin (Seq. I.D. No. 2) as well as N-terminal calreticulin fragments were prepared and tested to determine how these components were retained over an affinity column. To prepare the affinity column, three peptides were synthesized (KLGFFRR, Seq. I.D. 13; KAFFKR, Seq. I.D. No. 33; and KVFFKR, Seq. I.D. No. 32), purified, and coupled to CNBr-activated Sepharose 4B (Pharmacia). First, the ability of calreticulin, purified from the culture supernatant of the lymphoblastoid cell line VDS-O, to selectively bind to the column and be eluted by a buffer solution containing 20 mM EDTA and 100 mM NaCl, was verified. The purified preparations of VDS-O cell line containing both full length as well as N-terminal calreticulin fragments were then loaded on the column (Starting material). As shown in FIG. 18 full length calreticulin present in the material loaded was retained by the column and could be eluted with 20 mM EDTA, whereas the calreticulin fragments were found in the flow-through. These calreticulin fragments were subsequently found to be biologically active. Thus, the binding to the peptide sequence $KXaa_1FFXaa_2R$ (Seq. I.D. No. 11) or the sequence $KXaa_1GFFKR$ (Seq. I.D. No. 10) is not a property shared by calreticulin fragments that are active as inhibitors of endothelial cells growth and, moreover, the results suggest that $KXaa_1FFXaa_2R$ (Seq. I.D. No. 11) and $KXaa_1GFFKR$ (Seq. I.D. No. 10) are not part of a calreticulin receptor on endothelial cells.

To address this issue further, recombinant MBP-calreticulin fragment 120-180 (Seq. I.D. No. 5) was tested for its ability to bind to the affinity column described supra. Unlike MBP-calreticulin (Seq. I.D. No. 3) that bound to the column, the N-terminal calreticulin fragment (Seq. I.D. No. 5) failed to bind and was recovered in the flow-through.

The foregoing sections describe how the three newly discovered activities of calreticulin and calreticulin fragments were identified. The following Examples provide further guidance to one of skill in the art with respect to the production of calreticulin and calreticulin fragments and variant proteins, as well as the pharmaceutical formulation and administration of these proteins.

EXAMPLES

Example 1

Expression and Purification of Calreticulin and Calreticulin Fragments

Calreticulin may be purified from the supernatant of Epstein-Barr virus (EBV)-immortalized cell lines as described above. Calreticulin may also be purified from a tissue source using conventional biochemical techniques, or produced recombinantly in either prokaryotic or eukaryotic cells using methods well-known in the art (for example, those described in Sambrook et al., *Molecular Cloning: A Laboratory Manual*, Cold Spring Harbor, N.Y., 1989). The recombinant expression of calreticulin and the 180 amino acid N-terminal fragment are described in Singh et al. (*Proc. Natl. Acad. Sci. U.S.A.* 91:12770-12774, 1994) and Atreya et al. (*J. Viroli.* 69:3848-3851, 1995), respectively. Furthermore, the nucleic acid sequences encoding calreticulin are available on GenBank, and include the cDNA sequence shown in Seq. I.D. No. 1.

Recombinant expression of calreticulin and calreticulin fragments may be conveniently obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli.* and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column. Eukaryotic expression systems may also be employed, including Pichia, tobacco and Baculovirus expression systems, such as those available commercially from Invitrogen.

For each of these systems, the entire calreticulin protein may be produced by ligating the open reading frame (ORF) of calreticulin into the vector. To ensure effective expression, the ORF must be operably linked to the vector, i.e., must be joined such that the reading frame of the ORF is aligned with the reading frame of the protein tag. Where fragments of calreticulin are to be expressed, an ORF encoding the desired fragment may be amplified by polymerase chain reaction (PCR) from the calreticulin cDNA, cloned, purified and then ligated into the expression vector. Alternatively, the amplified fragment may be ligated directly into the expression vector. It may also be possible, depending on the availability of suitable restriction sites in the calreticulin cDNA to obtain the desired fragment by appropriate restriction endonuclease digestion, such that it can be directly cloned into the expression vector.

Purification of the expressed protein can be achieved either using the purification regimen appropriate for the expression tag (if a commercial expression/purification system is used), or conventional affinity chromatography using antibodies, preferably monoclonal antibodies, that recognize the appropriate regions of calreticulin may be employed.

Where calreticulin fragments are to be used, such fragments may alternatively be generated through digestion of the full-length calreticulin protein with various proteases. The fragments may then be separated based on their unique size, charge or other characteristics. Calreticulin fragments may also be synthetically generated through the use of known peptide synthesis methods.

Example 2

Assessing Therapeutic Activity

Following the purification of calreticulin or a fragment of calreticulin, the biological activity can be assessed using the methods described above. Specifically, the bFGF-induced endothelial cell proliferation assay can be used to determine endothelial cell inhibition, the Matrigel assay can be used to measure the inhibition of angiogenesis, and the athymic mouse/human Burkitt lymphomas model can be used to quantitate tumor inhibition.

When testing a calreticulin or calreticulin fragment preparation for activity, the bFGF-induced endothelial cell proliferation assay is generally first used. One skilled in the art will appreciate that this assay yields relatively quick results at relatively low cost.

Example 3

Calreticulin Sequence Variants

While the amino acid sequence of the prototypical human calreticulin protein is provided in Seq. I.D. No. 2, and the sequence of a cDNA molecule encoding this protein is given in Seq. I.D. No. 6, one of skill in the art will appreciate that the practice of this invention is not limited to these precise sequences. Thus, the invention may be practiced with molecules that differ from the exact molecules disclosed, but which retain the requisite biological activity.

Furthermore, variants of calreticulin and fragments of calreticulin that have been modified such that they do not bind to the amino acid motif described supra are of particular interest. These variants will retain the ability to specifically bind to endothelial cells, but will not be capable of binding the amino acid sequences shown in Seq. I.D. Nos. 11 and/or 10. This amino acid sequence motif is found in a family of steroid receptors (glucocorticoid, mineralcorticoid, progesterone and androgen receptors: KVFFKR, Seq. I.D. No. 32; estrogen receptor: KAFFKR, Seq. I.D. No. 33; thyroid hormone receptor: KSFFRR, Seq. I.D. No. 34; and retinoic acid receptor: KGFFRR, Seq. I.D. 35). Furthermore, it is also likely that therapeutically active variants and fragments of calreticulin do not bind to the consensus sequences shown in Seq. I.D. Nos. 10 and 11. A specific example of a naturally occurring sequence that falls into the integrin consensus sequence Seq. I.D. No. 10, is shown in Seq. I.D. No. 13. However, it is foreseeable that a calreticulin variant or fragment, that does not bind to the consensus sequences shown in Seq. I.D. Nos. 10 and 11, may be used in combination with full length calreticulin or a derivative of calreticulin that does bind to Seq. I.D. Nos. 10 and 11.

As mentioned above, the fragments and variants of calreticulin described supra, are characterized by their ability to inhibit endothelial cell growth, angiogenesis, and/or tumor growth. These abilities, however, are further defined as at least 30% inhibition of endothelial cell growth, angiogenesis, and/or tumor growth. However, it is likely that some therapeutically active fragments and variants of calreticulin will show an increased level of one or more of these biological activities. For example, some variants and fragments of calreticulin will show at least 40% inhibition, at least 50% inhibition, at least 60% inhibition, or at least 70% inhibition. Moreover, using the assays described above it is now possible to individually assess the biological activity of a given variant or fragment of calreticulin.

The therapeutically effective fragments and variants of calreticulin are also characterized by the number of amino acid residues that they contain. For example, in some instances it may be desirable to use relatively short fragments and variants of calreticulin. These short fragments and variants of calreticulin may contain at least 5, 10, 20, or 30 contiguous amino acids residues of the calreticulin sequence. However, such short fragments and variants of calreticulin will maintain at least one of the biological activities described supra.

Additionally, it is possible to vary the cDNA sequences encoding therapeutically effective fragments or variants of calreticulin while still encoding a protein having the desired biological activity. In their simplest form, such sequence variants may differ from the disclosed sequences by alteration of the coding region to fit the codon usage bias of the particular organism into which the molecule is to be introduced. Additionally, the coding region may be altered by taking advantage of the degeneracy of the genetic code to alter the coding sequence in such a way that, while the nucleotide sequence is substantially altered, it nevertheless encodes a protein having an amino acid sequence identical or substantially similar to the disclosed calreticulin protein sequence. For example, the first amino acid residue of the mature calreticulin protein is glutamic acid (Glu, E). This is encoded in the calreticulin open reading frame (ORF) by the nucleotide codon triplet GAG. Because of the degeneracy of the genetic code, one other nucleotide codon, GAA, also encodes for glutamic acid. Thus, the nucleotide sequence of the calreticulin ORF could be changed at this position to GAA without affecting the amino acid composition of the encoded protein or the characteristics of the protein.

As previously mentioned, the invention may also be practiced with calreticulin and calreticulin fragments that vary in amino acid sequence from the sequence shown in Seq. I.D. No. 2 (i.e. peptides that have been modified such that they do not bind to the consensus sequences described supra (Seq. I.D. Nos. 10 and 11). Variant calreticulin proteins include proteins that differ in amino acid sequence from the endogenous calreticulin sequence disclosed but which retain the specified biological activity. Such proteins may be produced by manipulating the nucleotide sequence of ORF that encodes the protein, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 6 shows amino acids which may be substituted for an original amino acid in a protein and which are regarded as conservative substitutions.

TABLE 6

| Original Residue | Conservative Substitutions |
|---|---|
| Ala | ser |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in function or other features may be obtained by selecting substitutions that are less conservative than those in Table 4, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the biological assays described above.

Example 4

Incorporation of Therapeutically Effective Fragments and Variants of Calreticulin into Pharmaceutical Compositions For administration to animals, purified calreticulin or calreticulin fragments are generally combined with a pharmaceutically acceptable carrier. Pharmaceutical preparations may contain only calreticulin or a single calreticulin fragment, or may be composed of calreticulin combined with one or more calreticulin fragments, or may be composed of multiple calreticulin fragments. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, human albumin or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals may be only inefficiently delivered through ingestion. However, pill-based forms of pharmaceutical proteins may be alternatively be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

It is also contemplated that calreticulin could be delivered to cells in the nucleic acid form and subsequently translated by the host cell. This could be done, for example through the use of viral vectors or liposomes. Liposomes could also be used for the delivery of the protein itself.

The therapeutically effective fragments may also be delivered in conjunction with other therapeutic agents. These additional therapeutic agents can be angiogenesis inhibitors such as, platelet-factor-4, IP-10 (interferon (IFN)-γ inducible protein-10), MIG (Monokine induced by IFN-γ), IFN-α, angiostatin, endostatin, fumagillin, AGM-1470, thrombospondin, a fragment of prolactin, antibody against the integrin $\alpha_v\beta_3$, IL-12, cleaved conformation of the serpin antithrombin thalidomide and mixtures thereof. The additional therapeutics could also be chemotherapeutics, hormones, anti-inflammatory agents, antibiotics and/or anti-viral agents.

The pharmaceutical compositions of the present invention may be administered by any means that achieve their intended purpose. Amounts and regimens for the administration of calreticulin, or a therapeutically active fragment thereof, can be determined readily by those with ordinary skill in the clinical art of treating diseases associated with angiogenesis, endothelial cell growth and/or tumor growth. For use in treating these conditions, the described proteins are administered in an amount effective to inhibit angiogenesis, endothelial cell growth and/or tumor growth. The peptides or proteins may be administered to a host in vivo, such as for example, through systemic administration, such as intravenous or intraperitoneal administration. Also, the peptides or proteins may be administered intralesionally: i.e. the peptide or protein is injected directly into the tumor or affected area.

Effective doses of calreticulin and calreticulin fragments for therapeutic application will vary depending on the nature and severity of the condition to be treated, the age and condition of the subject and other clinical factors. Thus, the final determination of the appropriate treatment regimen will be made by the attending clinician. Typically, the dose range will be from about 0.1 µg/kg body weight to about 100 mg/kg body weight. Other suitable ranges include doses of from about 1 µg/kg to 10 mg/kg body weight. The dosing schedule may vary from once a week to daily depending on a number of clinical factors, such as the subject's sensitivity to the protein. Examples of dosing schedules are 3 µg/kg administered twice a week, three times a week or daily; a dose of 7 µg/kg twice a week, three times a week or daily; a dose of 10 µg/kg twice a week, three times a week or daily; or a dose of 30 µg/kg twice a week, three times a week or daily. In the case of a more aggressive disease it may be preferable to administer doses such as those described above by alternate routes including intravenously or intrathecally. Continuous infusion may also be appropriate.

As mentioned above calreticulin and calreticulin fragments will be useful for the treatment of diseases associated with unwanted angiogenesis. Angiogenesis is commonly associated with ocular diseases. Some of these diseases are, retrolental fibroplasia, trachoma, retinal neovascularization, macular degeneration, diabetic retinopathy and neovascular glaucoma, corneal graft rejection and contact lens overwear. Other non-ocular diseases, which are associated with unwanted angiogenesis, can also be treated with calreticulin and fragments of calreticulin. Examples of such diseases are, periodontal disease, psoriasis, angiofibromas, immune-inflammation, atherosclerosis, excessive wound repair, non-immune inflammation, Crohn's disease, and systemic lupus. Examples of diseases that are associated with immune-inflammation are rheumatoid arthritis, systemic lupus erythematosus, thyroiditis, Goodpasture's Syndrome, systemic vasculitis, scleroderma, Sjogren's syndrome, sarcoidosis or primary biliary cirrhosis.

Calreticulin and fragments of calreticulin may also be useful for the treatment diseases with unknown etiology, for example, Kaposi's sarcoma.

In addition to being used for the treatment of disease, calreticulin and fragments of calreticulin, may be useful as preventative agents. For instance, calreticulin may be useful as a preventative of pregnancy by inhibiting angiogenesis at the site of implantation. Calreticulin and the effective fragments might also be used as a preventative of injury from radiation and/or chemotherapy. Used in this way the therapeutically active fragments or variants would be administered prior to the radiation and/or chemotherapy treatment and the resulting inhibition of angiogenesis would serve to protect hematopoietic cells from injury.

Calreticulin and calreticulin fragments can also be used to treat a variety of malignancies and related disorders, such as leukemias, including acute leukemias (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrdm's macroglobulinemia, heavy chain disease), as well as solid tumors such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). As stated above the precise details of the clinical treatment will depend on the specific tumor type and the severity of the condition.

Furthermore, calreticulin and fragments of calreticulin have been shown to inhibit angiogenesis which is induced by basic fibroblast growth factor (see endothelial cell proliferation assay discussed above). Therefore, one of ordinary skill will appreciate that calreticulin and fragments of calreticulin will also inhibit angiogenesis, which is induced by other compounds. These angiogenesis inducing compounds could be for example, acidic fibroblast growth factor, Vascular Endothelial Growth Factor (VEGF), hepatocyte growth factor, Interleukin (IL)-15, IL-12, IL-8, platelet-derived endothelial cell growth factor (PDECGF), angiogenin, Transforming Growth Factor (TGF)-β, Tumor necrosis Factor (TNF)α, and angiogenin.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

---

We claim:

1. A method of inhibiting growth of a tumor in a subject, comprising:

selecting a subject having a tumor; and administering to the subject having a tumor a therapeutically effective amount of a polypeptide comprising an amino acid sequence at least 95% homologous to the amino acid sequence as set forth in SEQ ID NO: 2, or a therapeutically effective fragment thereof, wherein the polypeptide or therapeutically effective fragment thereof inhibits growth of the tumor in the subject.

2. The method of claim 1, wherein the polypeptide is administered in a composition comprising a pharmaceutically acceptable carrier.

3. The method of claim 1, wherein the therapeutically effective fragment comprises the amino acid sequence as set forth in SEQ ID NO: 6.

4. The method of claim 1, wherein the therapeutically effective fragment comprises the amino acid sequence as set forth in SEQ ID NO: 8.

5. The method of claim 1, wherein the therapeutically effective fragment comprises the amino acid sequence as set forth in SEQ ID NO: 5.

6. The method of claim 1, wherein the therapeutically effective fragment comprises the amino acid sequence as set forth in SEQ ID NO: 4.

7. The method of claim 1, wherein the therapeutically effective fragment comprises the amino acid sequence as set forth in SEQ ID NO: 9.

8. The method of claim 1, wherein the therapeutically effective fragment comprises the amino acid sequence as set forth in SEQ ID NO: 3.

9. The method of claim 1, wherein the polypeptide comprises an amino acid sequence at least 95% homologous to the amino acid sequence as set forth in SEQ ID NO: 2.

10. The method of claim 9, wherein the polypeptide comprises an amino acid sequence at least 98% homologous to the amino acid sequence as set forth in SEQ ID NO: 2.

11. The method of claim 10, wherein the polypeptide comprises the amino acid sequence as set forth in SEQ ID NO: 2.

12. The method of claim 1, wherein the tumor comprises a colon carcinoma, a breast adenocarcinoma, a neuroblastoma, a Wilms tumor, a rhabdomyosarcoma, an acute lymphocytic leukemia, an acute promyelocytic leukemia, a promyelomonocytic lymphoma, a Burkitt lymphoma, a lung adenocarcinoma, or a melanoma.

13. The method of claim 1, wherein the tumor is a carcinoma.

14. The method of claim 1, wherein the tumor is a leukemia.

15. The method of claim 6, further comprising administering a therapeutically effective amount of interleukin-12.

* * * * *